United States Patent
Ferrari et al.

(10) Patent No.: US 6,190,357 B1
(45) Date of Patent: Feb. 20, 2001

(54) EXPANDABLE CANNULA FOR PERFORMING CARDIOPULMONARY BYPASS AND METHOD FOR USING SAME

(75) Inventors: Richard M. Ferrari, Saratoga; Dwight P. Morejohn, Davis; Ivan Sepetka, Los Altos; Robert C. Glines, Cameron Park, all of CA (US)

(73) Assignee: Cardiothoracic Systems, Inc., Cupertino, CA (US)

( * ) Notice: Under 35 U.S.C. 154(b), the term of this patent shall be extended for 0 days.

(21) Appl. No.: 09/063,588

(22) Filed: Apr. 21, 1998

(51) Int. Cl.$^7$ ................................................ A61M 29/00
(52) U.S. Cl. ............................... 604/102.01; 604/96.01; 604/523
(58) Field of Search ........................... 604/96, 104, 264, 604/171, 523, 96.01, 102.01

(56) References Cited

U.S. PATENT DOCUMENTS

| | | | |
|---|---|---|---|
| 4,141,364 | 2/1979 | Schultze | 128/349 |
| 4,479,497 | 10/1984 | Fogarty et al. | 128/344 |
| 4,589,868 | 5/1986 | Dretler | 604/96 |
| 4,601,713 | 7/1986 | Fuqua | 604/280 |
| 4,738,666 | 4/1988 | Fuqua | 604/280 |
| 4,846,791 | 7/1989 | Hattler et al. | 604/43 |
| 4,896,669 | 1/1990 | Bhate et al. | 606/194 |
| 4,955,895 | 9/1990 | Suglyama et al. | 606/194 |
| 5,176,659 | 1/1993 | Mancini | 604/280 |
| 5,183,464 | 2/1993 | Dubrul et al. | 128/3 |
| 5,234,425 | 8/1993 | Fogarty et al. | 606/1 |
| 5,425,708 | 6/1995 | Nasu | 604/96 |
| 5,452,733 | 9/1995 | Sterman et al. | 128/898 |
| 5,573,508 | 11/1996 | Thornton | 604/96 |
| 5,573,509 | 11/1996 | Thornton | 604/102 |
| 5,573,517 | 11/1996 | Bonutti et al. | 604/264 |
| 5,584,803 | 12/1996 | Stevens et al. | 604/4 |
| 5,601,590 | 2/1997 | Bonutti et al. | 606/192 |
| 5,674,240 | 10/1997 | Bonutti et al. | 606/198 |
| 5,707,354 | 1/1998 | Salmon et al. | 604/96 |
| 5,755,687 | 5/1998 | Donlon | 604/53 |
| 5,810,721 | 9/1998 | Mueller et al. | 600/206 |
| 5,827,243 | * 10/1998 | Palestrant | 604/282 |

FOREIGN PATENT DOCUMENTS 0 385 920   5/1990  (EP) .

* cited by examiner

*Primary Examiner*—Sharon Kennedy
*Assistant Examiner*—Cris L. Rodriguez
(74) *Attorney, Agent, or Firm*—Limbach & Limbach LLP

(57) ABSTRACT

A device for occlusion of a body passageway and subsequent perfusion of the body passageway with arterial return blood, cardioplegia and other fluid is disclosed. The device of the present invention is an expandable cannula comprising a flexible, expandable tubular elongate body having a first diameter and a second diameter, wherein the expandable cannula is inserted having a first diameter and then expanded to a second diameter to provide perfusion flow to the body passageway through at least one arterial return aperture provided on the distal end of the expandable tubular elongate body in fluid communication with a perfusion lumen provided within the cannula. The device may be further provided with one or more additional lumens for providing additional functions to the vessel lumen and may also include an expandable occluding member fixed at the distal end of the cannula for isolating the surgical area from the rest of the arterial system. A preferred method of use of the present invention is also disclosed wherein having a first diameter is inserted endovascularly into the vessel of a patient and advanced to a point of interest. At the point of interest, the device is expanded to a second diameter and perfusion flow to the vessel lumen is provided. Following the performance of a surgical procedure, perfusion flow is terminated and the device is removed from the vessel.

6 Claims, 12 Drawing Sheets

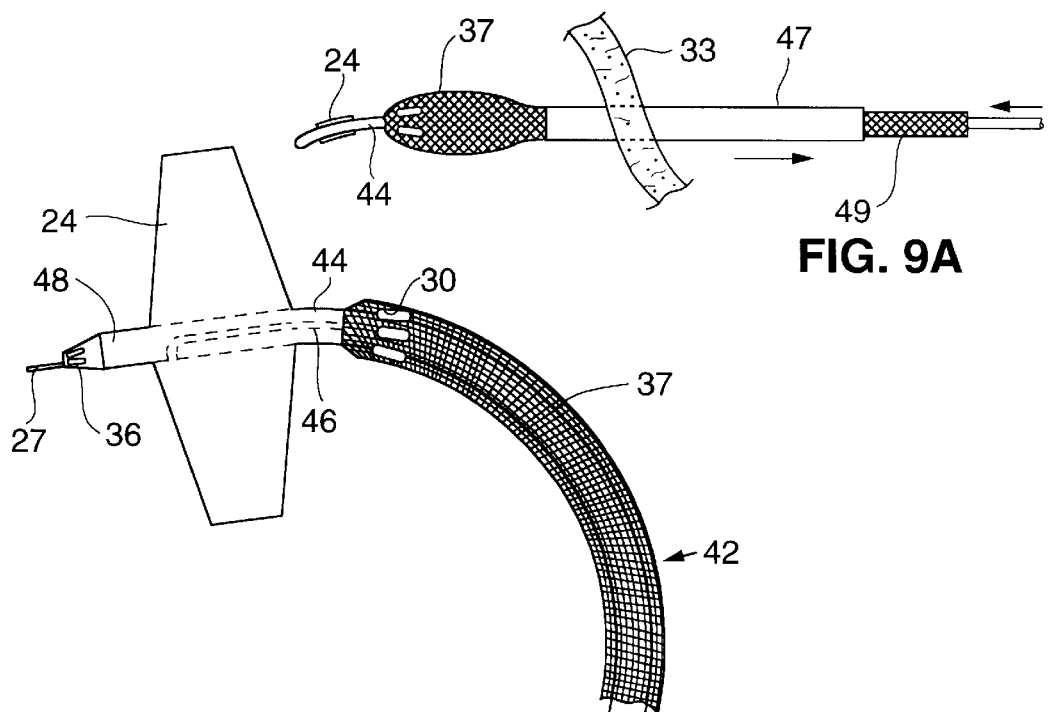
FIG. 9A
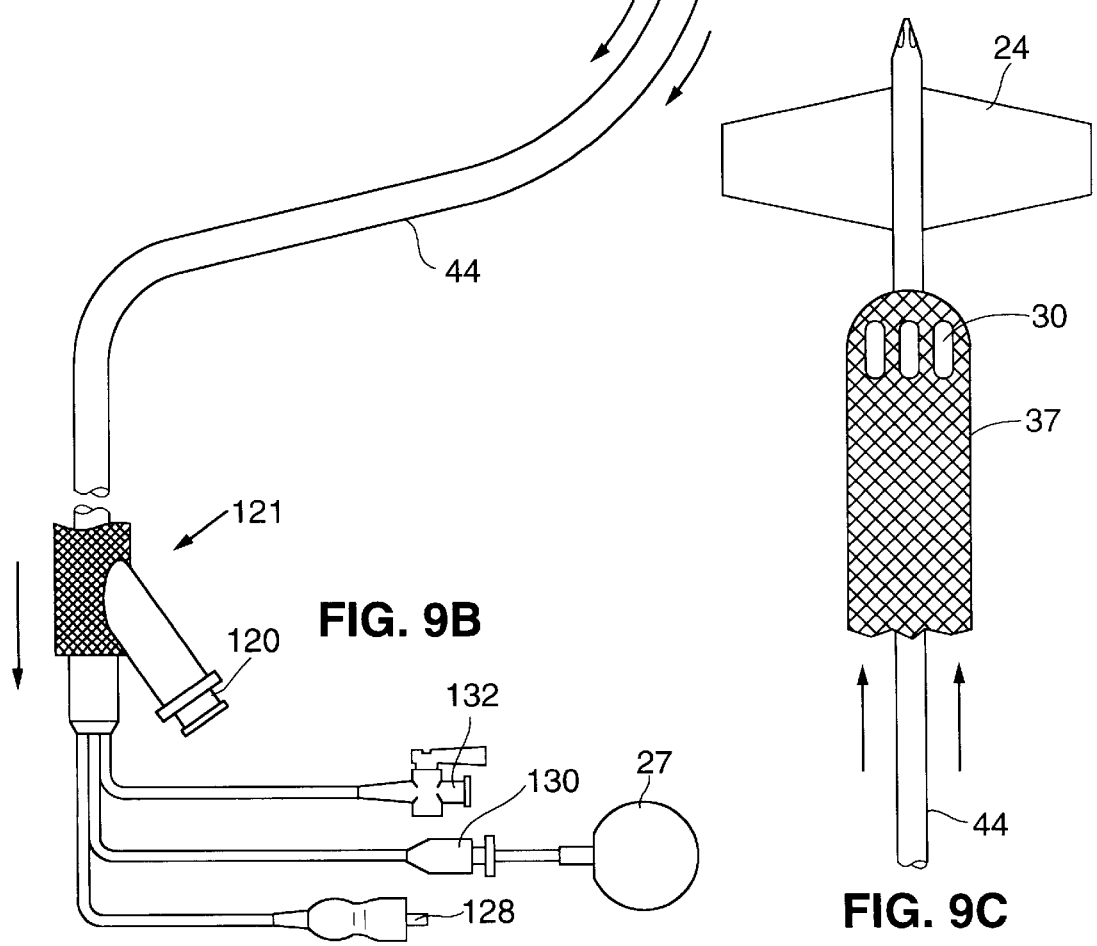
FIG. 9B
FIG. 9C

EXPANDABLE CANNULA FOR PERFORMING CARDIOPULMONARY BYPASS AND METHOD FOR USING SAME

FIELD OF THE INVENTION

This invention relates to devices for the occlusion of blood vessels, more particularly to the occlusion and subsequent perfusion, cardioplegia or venting of blood vessels using a cannula endovascularly inserted within the lumen of the vessel. The system is well suited for occlusion and perfusion of the aortic arch or major arteries during cardiopulmonary bypass procedures.

BACKGROUND OF THE INVENTION

Cardiac surgery often requires that the heart be stilled during the procedure. An arrested heart allows the surgeon sufficient time and a stable environment on which to operate, a particular necessity for lengthy and invasive procedures such as valve replacement. A number of devices and procedures have been developed to enable a physician to stop the heart long enough for a surgical procedure to be performed, and then restart the heart at the termination of the procedure.

Stopped heart procedures are complex and often cause patient trauma during the procedure and during post-operative recovery. Over the years, the application and effectiveness of stopped heart procedures have increased, meanwhile attempts have been made to limit patient trauma recovery time, and overall expense.

To maintain the flow of oxygenated blood during a stopped heart procedure, the heart and lungs must be bypassed during the time that the heart is stopped. This by pass us achieved using a cardiopulmonary bypass (CPB) apparatus. The essential goals of CPB for heart surgery are to provide life-support functions, a motionless, decompressed heart, and a dry, bloodless field of view for the surgeon. In a basic CPB system, the heart is stopped by the infusion of cardioplegia. Oxygen-poor blood is drained by gravity or suctioned from the patient's venous circulation, and is transported to a pump-oxygenator, commonly known as the heart-lung machine, where the blood is exposed to a gaseous mixture that eliminates carbon dioxide and adds oxygen. The venous drainage process may involve placement of a cannula (or cannulae) into the right side of the heart (typically the right atrium), or directly in the major veins (typically the superior vena cava (SVC) and/or inferior vena cava (IVC) or through peripheral vein access sites. An arterial or aortic perfusion cannula is placed in the aorta or another large peripheral artery, such as the common femoral artery, to return oxygenated blood to the patient.

Cardioplegic arrest and CPB are commonly employed during cardiac surgery for treating coronary artery disease and heart valve disease. In coronary artery disease, a buildup of stenotic plaque in the coronary arteries causes the artery to narrow or become occluded. The interruption of the blood flow to the heart causes myocardial infarction, commonly known as a heart attack. Heart valve disease includes two major categories, namely valvular stenosis, which is an obstruction to forward blood flow through the heart valve, and regurgitation, which is the retrograde leakage of blood through the heart valve. Most commonly, valvular stenosis occurs in the aortic valve while regurgitation is typically a congenital condition affecting the mitral valve.

Typically, after the patient's chest has been opened through either a thoracotomy or a sternotomy, a cannula will be inserted into the patient's aortic arch. The insertion of the arterial (aortic) perfusion cannula is usually performed in the following fashion. After the patient's chest has been opened and the pericardium (the protective sac around the heart) has been entered, two concentric purse string sutures are placed into the anterior wall of the ascending aorta just proximal to upstream side of the brachiocephalic trunk. A "choker" tube or sleeve is positioned over the trailing ends of the suture threads to act as a tourniquet for tightening the purse string suture. A small incision is then made through the wall of the aorta in the center of the purse-string sutures. The aortic perfusion cannula is then quickly inserted through that incision into the aorta, taking care to minimize the escape of blood from the puncture site. The purse string sutures are then tightened by means of their respective tourniquets to seal the aortic wall around the perfusion cannula in order to prevent the escape of blood from the aorta. Air is then purged by arterial pressure from the perfusion cannula which is in fluid communication with the pump-oxygenator. A cross-clamp is placed on the aorta just downstream of the aortic root and upstream of the cannula to ensure that no blood flows back toward the aortic valve during CPB.

After CPB has been established, cardioplegia is administered by delivering a cardioplegic solution, such as potassium, magnesium, procaine, or a hypocalcemic solution, to the myocardium by one or a combination of two general techniques, antegrade and retrograde perfusion. Antegrade perfusion of cardioplegia involves the infusion of fluid through the coronary arteries in the normal direction of blood flow. A cannula is typically inserted into the aorta upstream of the aortic clamp and the solution is injected into the aortic root and delivered under pressure in the normal direction of blood flow into the coronary ostia and from there to the myocardium. For procedures on the aortic valve, cardioplegia is typically administered via a transverse aortotomy whereby direct access to the coronary ostia is possible. The cardioplegia is delivered using a wand inserted intermittently into the ostia during the procedure. Retrograde perfusion is accomplished by inserting an occlusion into the coronary sinus and administering cardioplegia upstream of the occlusion and forcing the fluid against the normal flow of the blood into the coronary veins to the myocardial capillary beds.

Once the beating of the heart has been arrested, the surgeon will perform the necessary coronary procedures and repairs. When these repairs have been completed, the arterial and venous cannula will be removed from the surgical area and the entrance sutures tightened to seal the vessel punctures.

The placement of the occluder in the ascending aorta is a particularly delicate operation as the operator must take care so as to not block the left subclavian artery, the brachiocephalic artery, or the left carotid artery, but must instead occlude the aorta just upstream of these aortic branches. Even if the placement of the occluder is proper at the initiation of the coronary repair procedure, the position of the device should be monitored closely to avoid even slight movement as the procedure continues. Movement of the device may result in partial or total closure of the aortic branches, depriving the upper body and brain of the patient of blood during the procedure. Similarly, movement toward the aortic valve and/or the left ventricle of the patient should be avoided to prevent damaging the valve. It would thus be desirable to have a system which could allow imaging of the interior of the vessel to determine proper placement of the cannula within the vessel and to enable imaging of the interior of the vessel intermittently during a procedure.

The design of an endovascularly inserted cannulae must take into account the limited space available in the body passageways used for access to the heart and other regions of interest. The use of multiple cannulae increases the number of percutaneous or direct cut-down procedures required for the procedure and increases the risk or infection and other post-operative complications. Multiple insertions also increase the risk of damage to the internal vasculature and increase the complication and time expenditure for the procedure. It would be most desirable to provide a system which would combine a multitude of functions in one device so that the need for multiple or duplicative devices can be avoided.

The device should have a minimal small cross-sectional diameter to reduce the risk of patient trauma. Particularly with patients having advanced heart disease, scaling and calcium deposits are common on the interior of the femoral and iliac artery and the aorta and the use of large diameter cannula increases the risk of dislodging this stenotic plaque, calcium deposits, and other material that has accumulated on the wall of the vessel. The problem is particularly acute when the femoral artery is accessed as the cannula is advanced against the direction of normal blood flow and consequently against the direction of scaling and accumulation of material on the arterial wall. Viability of the femoral artery may also prove to be problematic when using endovascular insertion of a cannula into the aortic arch. Vessels with an insufficient diameter for the introduction of the cannula assembly, either naturally occurring or through vessel stenosis, can prevent the use of such a system unless some alternate means of arterial or venous access to the region of interest is found.

Regardless of the condition of the vessel pathway, endovascular insertion of a cannula around 80 cm in length into a patient's vascular system is complicated and difficult and may be rendered impossible by the bends, branches, or diseased condition of the vessels of the patient. A cannula system that uses alternate access pathways to the heart and other regions of interest would be desirable. Typically, past procedures have used the femoral artery, the femoral vein, and the jugular vein for coronary access because these are the only vessels with sufficient diameter to accommodate a cannula of the appropriate diameter for cardiac repair and other procedures. A device which could access the heart via smaller pathways, such as the right and left subclavian veins or the left subclavian artery, would be desirable because these pathways provide a shorter and less tortuous path to the region of interest. Also, the use of the left subclavian artery, for example, would help prevent severe brain embolism as any dislodged plague from the artery would most likely pass into the subclavian artery or the descending aorta and then into an arm, leg or abdominal viscera of the patient. Ideally, both endovascular and transvascular insertion of the cannula would be possible.

Access via an abdominal aorta incision, a direct aortic arch stick via an endoscopic trocar, a minimally invasive para-sternotomy or mini-sternotomy or thoracotomy, a central access full sternotomy, or an approach through either atrium and through the mitral and aortic valves would are other applications for an improved cannula in addition to the endovascular applications discussed above. Use of alternate pathways thus would limit the risk of embolic material traveling into either carotid and into the brain.

It is therefore highly desirable to have a system which can be used for minimally invasive surgery to isolate the heart and its coronary arteries from the rest of the arterial system. It is also desirable that the system minimizes the risks of embolism and other complications associated with traditional aortic occlusion techniques. The system would preferably allow multiple functions within a single device to limit obstruction of the surgical field and reduce patient trauma and procedure time. The device should also preferably be of a size which would allow use in multiple venous and arterial access sites.

SUMMARY OF THE INVENTION

Briefly, the present invention provides an improved apparatus and method for occluding a blood vessel as part of a surgical procedure, for example, occluding the aorta during cardiopulmonary bypass. In a preferred embodiment, a cannula is provided comprising a flexible, expandable tubular elongate body wherein the tubular elongate body is expandable from a first diameter to a second diameter. The cannula is introduced into a body passageway having a first diameter and is then expanded to a second diameter in order to provide better fluid flow into the body passageway. A perfusion lumen is provided within the expandable tubular elongate body with at least one arterial return aperture provided within the tubular elongate body in fluid communication with the perfusion lumen.

The cannula may also include an expandable member fixed at the distal end of the tubular elongate body. The expandable member is configured to occlude the body passageway when expanded in order to provide a clear surgical field upstream of the occlusion or a sealed chamber in which to inject the cardioplegia fluid. The expandable member may be configured from polyurethane, PVC, PET or other similar materials. In one preferred embodiment, the expandable member is an inflatable while in another, the expandable member is a low density foam about which is disposed a fluid impermeable membrane fixing the expandable member to the distal end of the cannula.

Additional lumens may be provided within the device. The device of the present invention may include an inflation lumen for an expandable member, a multi-purpose lumen for imaging, cardioplegia, venting, or guidewire and tool access to the vessel lumen, a pressure monitoring lumen for pressure monitoring of the vessel, or a dedicated cardioplegia lumen.

A preferred embodiment of the present invention is configured having an inner tubular elongate body, an outer expandable tubular elongate body expandable from a first to a second diameter, wherein the outer tubular elongate body substantially disposed about the inner tubular elongate body, the inner tubular elongate body and the outer tubular elongate body cooperating to form a perfusion lumen therebetween. The inner tubular elongate body is configured having one or more lumens therein to provide cardioplegia, venting, tool access, and other functions to the vessel lumen. The main perfusion lumen also includes at least one arterial return aperture provided in the outer expandable tubular elongate body. A preferred embodiment includes an expandable member disposed at the distal end of the cannula for occlusion of the vessel lumen.

A preferred embodiment includes means for expanding the outer expandable tubular elongate body from the first diameter to the second diameter. Such means include disposing the expandable tubular elongate body within a sheath during insertion of the cannula in a first diameter and then removing the sheath to expand the cannula to a second diameter. Additional expansion means include subjecting the perfusion lumen to a vacuum source during insertion of the device and removing the vacuum prior to providing perfusion flow to the vessel or fastening the expandable outer tubular elongate body on itself during insertion. Preferred embodiments are disclosed wherein the arterial return apertures include a one-way valve to allow the maintenance of a vacuum on the perfusion lumen while allowing subsequent perfusion of the vessel lumen.

Another preferred embodiment of the present invention is configured having walls of varying thickness so that the outer tubular elongate body is more readily collapsible at the circumferential locations having a thinner wall thickness. When collapsed, such a design provides a cannula having a decreased diameter and an increased column strength which allows unaided endovascular insertion of the contracted cannula.

A method of occluding a vessel passage and subsequently providing fluid flow to the passage is disclosed, the steps comprising making a percutaneous incision in the vessel to be accessed, inserting an expandable cannula into the body passageway, advancing the cannula to a region of interest in the body passageway, expanding the tubular elongate body of the expandable cannula to a second diameter greater than the first diameter, and providing fluid flow to the perfusion lumen of the expandable cannula which is in fluid communication with the vessel lumen. After the surgical procedure is complete, fluid flow to the vessel is terminated and the cannula is removed, allowing the percutaneous incision to be closed. The expandable cannula may also be contracted to a first diameter prior to removal of the cannula to aid in the removal of the cannula.

Access sites suitable for application of the device and methods of the present invention include the right and left femoral arteries, the aortic arch, the right and left subclavian, abdominal aorta access, access via either atrium through the mitral and aortic valves, or access through a full or mini-sternotomy. The regions of interest for which the device and methods of the present invention are well suited include the venous and arterial vessels of the heart, including the jugular veins, SVC, IVC, right atrium, and aortic arch, the mitral and aortic valves of the heart, and the peripheral vessels of the heart.

In a preferred method, an expandable member is expanded to occlude the body passageway upstream of the arterial return flow provided to the body passageway. Upon completion of the surgical procedure, the expandable member is contracted sufficiently to allow removal of the expandable cannula from the body passageway.

Additional steps of the present invention are also disclosed, including providing cardioplegia fluid to the body passage through a cardioplegia lumen provided within the expandable cannula; inserting a surgical tool into a tool lumen provided in the expandable cannula, performing a surgical procedure on the patient with the surgical tool, and removing the surgical tool; imaging the interior of the vessel lumen; and venting the vessel lumen.

BRIEF DESCRIPTION OF THE DRAWINGS

FIG. 9a is a configuration of the present invention wherein the outer tubular elongate body is a woven mesh material which contracts when stretched axially and expands when released.

FIG. 9b is an embodiment of the cannula FIG. 9a with the expandable braided sheath in an axially stretched first diameter.

FIG. 9c is the proximal end of the cannula of FIG. 9a showing a balloon occluder fully inflated and the expandable braided sheath in a relaxed second diameter

DETAILED DESCRIPTION OF THE INVENTION

As used herein, the terms "upstream" and "downstream" refer to areas closer to and farther from the heart in the arterial system, respectively. These directions are reversed when used to describe directions in the venous system of the heart. The terms proximal and distal refer to locations closer to and farther from the physician or person performing the procedure.

The invention will be described by reference to particular embodiments and applications for purposes of illustration. Obvious variations and equivalents of the disclosed invention will become apparent to one skilled in the art without departing from the subject matter defined by the appended claims and their equivalents.

Figure 1:
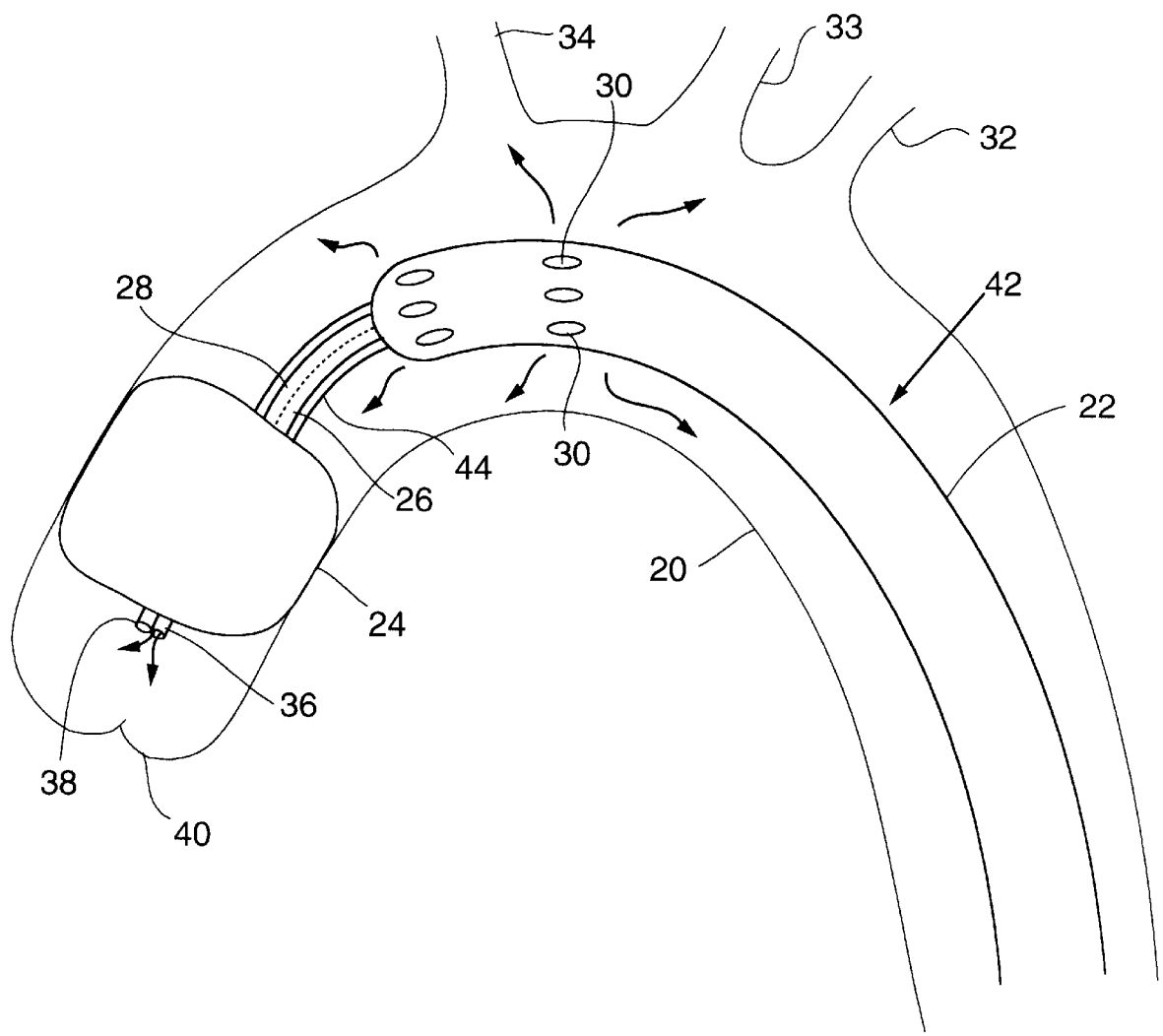
FIG. 1 is a cut-away of the aortic arch of a patient showing the device of the present invention in place in the aortic arch.

The device of the present invention is particularly well suited for cardiopulmonary bypass procedures (CPB). FIG. 1 shows one embodiment of the expandable cannula of the present invention endovascularly inserted into the aortic arch of a patient to perform CPB. The cannula 42 comprises an expandable outer tubular elongate body 22 disposed about an inner tubular elongate body 44. The internal tubular elongate body is provided with a tool lumen 38 and cardioplegia lumen 36 configured to provide cardioplegia to the right and left ostia of the coronary sinus. The tool lumen and the cardioplegia lumen may be alternatively configured as one multi-purpose lumen or lumen 38 may be used a pressure monitoring lumen.

The outer expandable tubular elongate body also includes a number of arterial return apertures 30 for providing perfusion to the interior of the aorta 20. In operation, a drainage cannula will be introduced into the right ventricle or other venous drainage site and the de-oxygenated blood will be drained from the body to an external CPB machine (not shown). The CPB machine will condition the blood, remove the carbon dioxide, and re-oxygenate the blood before returning it to the arterial system via the expandable cannula. The proximal end of the expandable cannula will thus be attached to the CPB machine so that the perfusion lumen is provided with arterial blood from the machine. The perfusion lumen will preferably be attached to the external source of arterial perfusion using a luer lock or other well known connection. Once the blood enters the proximal end of the perfusion lumen, it will travel through the lumen to the arterial return apertures 30 and from there into the arterial system. The apertures 30 are preferably configured so that arterial perfusion is provided at the aortic branches first wherein the excess flow will travel down the ascending aorta and into the arterial system for the lower extremities of the body.

The distal end of inner tubular elongate body 44 is also provided with an expandable member 24 which is expanded to occlude the aortic arch and insure a bloodless surgery field for a surgical procedure upstream of the expandable member 24 or a sealed chamber in which to administer cardioplegia. In a preferred embodiment, the expandable member 24 is a balloon made from polyurethane or other such material.

Polyurethane is well suited for this application as it has some resilience and will be suited for various sized vessel lumens to fit a variety of patients and applications and allow some adjustment of the member during a surgical procedure. in some applications, it may be desirable to have an expandable member which has a maximum diameter beyond which the member will burst so as to prevent accidental dissection or damage to the aorta of the patient. The balloon can be inflated with a saline fluid or other biologically acceptable fluid or gas introduced using an inflation lumen (not shown) provided within the inner tubular elongate body 44 or the outer expandable tubular elongate body 22. In use, the balloon is preferably positioned so that it is disposed between the brachiocephalic trunk and the coronary ostia.

Figure 2:
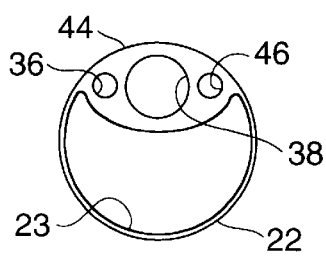
FIG. 2 is a cross-section of one embodiment of the present invention showing an alternative configuration of the internal lumen of the device.

Specific cross-sectional configurations will now be described with reference to the attached figures. FIG. 2 shows one cross section of an expandable cannula embodiment. The cannula comprises a inner tubular elongate body 44 which is integrally formed with the outer expandable tubular elongate body 22. A number of lumens can be integrally formed within the inner tubular elongate body 44, including a tool lumen or pressure monitoring lumen 38, a cardioplegia lumen 36 and an inflation lumen 46. Lumen 38 can also serve as a multi-function lumen for introduction of a guide wire (not shown) or other such devices, as well as venting of the vessel lumen.

The primary consideration for the design of the cannula is to provide a means whereby the cannula can be inserted at a first diameter to a point of interest in the vessel. Once the cannula is in place, the device may then be expanded to a second diameter to provide low velocity perfusion flow to the vessel at the correct pressure. Typically, the flow rate is between 3 and 3 liters/min. at a pump pressure of about 200 mm Hg. Because the perfusion lumen 23 is contracted during insertion of the cannula, the additional available cross-sectional profile may be used for other lumens so that additional functions may be performed by the cannula 42.

Figure 3A:
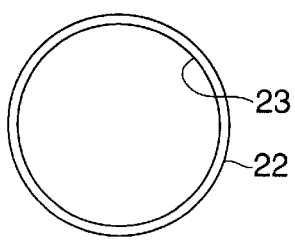
FIG. 3a is a cross-section of one embodiment of the present invention showing an alternative configuration having a single lumen with the device shown expanded to a second diameter.
Figure 3B:
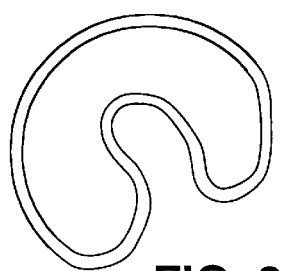
FIG. 3b is a cross-section of one embodiment of the present invention showing an alternative configuration having a single lumen with the device shown partly contracted between a first diameter and a second diameter.

To contract the outer expandable tubular elongate body 22 of FIG. 3, the member is folded over on itself to be in close proximity to the inner tubular elongate body 44. FIG. 3(a–c) show a single lumen expandable cannula as it is contracted from an expanded second diameter to its first diameter. Following the insertion of the cannula to a region of interest, the tubular elongate body is expanded to have a second diameter suited for providing perfusion flow to the arterial system.

Figure 3C:
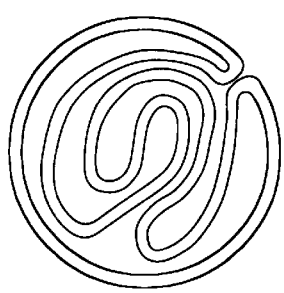
FIG. 3c is a cross-section of one embodiment of the present invention showing an alternative configuration having a single lumen with the device shown contracted to a first diameter and contained within a sheath.

Depending on the access site and the region of interest in which the cannula is disposed, a single lumen formed within the outer tubular elongate body (as seen in FIG. 3c) may not have sufficient column strength to allow insertion of the device into certain body vessels unaided. It may also be difficult to maintain the device in a furled or folded configuration during insertion of the member. To remedy these problems, an introducer sheath 58 as seen in FIGS. 12(a–d) may be used to augment the strength of the expandable outer elongate tubular elongate body and keep the expandable member furled in its first diameter. The sheath 58 is configured having a tubular elongate body with a lumen therethrough for introduction of the contracted expandable cannula. The distal end of the sheath may be shaped to allow easier insertion of the sheath and may include an atraumatic tip which will minimize damage from inadvertent contact with the vessel wall. The distal end is further configured to allow the deployment of the expandable cannula prior to providing perfusion flow to the body vessel.

In use, the sheath is introduced into the vessel to a point of interest and the expandable cannula is deployed from the distal end of the sheath. The sheath 58 can be simultaneously withdrawn during deployment of the expandable cannula to eliminate movement of the cannula 42 relative to the vessel wall. The sheath 58 may be made of any number of polymers, providing the polymer material has a durometer sufficiently high to remain semi-rigid with a thin-walled construction. Preferably it would also have a hemostatic seal at its distal end to prevent unnecessary loss of blood. Following perfusion of the vessel through the cannula, the cannula 42 is withdrawn into the sheath and the sheath 58 is removed from the body vessel.

Figure 11A:
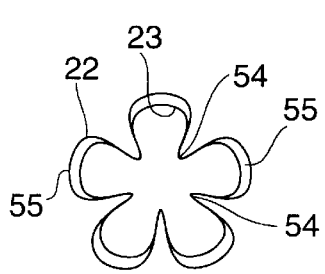
FIG. 11a is a cross-section of one embodiment of the present invention showing a configuration having a single lumen with the wall of the outer tubular elongate body having thinned wall portions acting as hinge portions for contraction of the outer tubular elongate body.
Figure 11B:
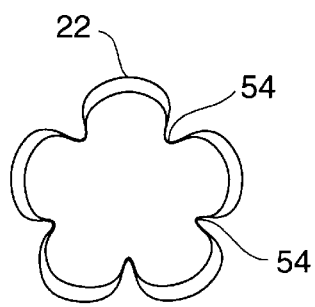
FIG. 11b is a cross-section of the device of FIG. 11a with the device shown partially expanded.
Figure 11C:
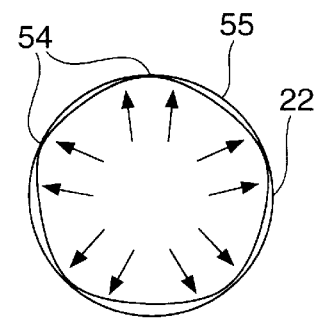
FIG. 11c is a cross-section of the device of FIG. 11a with the device shown expanded to a second diameter.
Figure 12A:
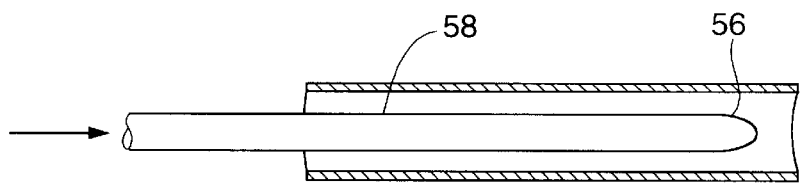
FIG. 12a shows the vessel of a patient with a cannula introduction sheath in place in the body vessel.
Figure 12B:
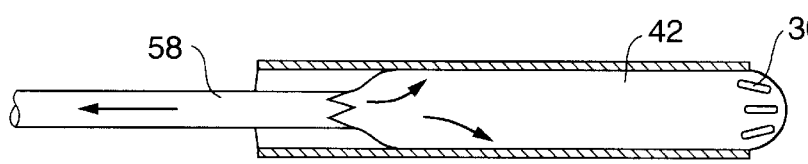
FIG. 12b shows the vessel of a patient with a cannula introduction sheath in place in the body vessel with the expandable cannula deployed in the vessel.
Figure 12C:
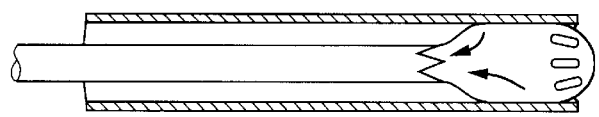
FIG. 12c shows the vessel of a patient with a cannula introduction sheath in place in the body vessel with the expandable cannula partially withdrawn into the sheath.
Figure 12D:
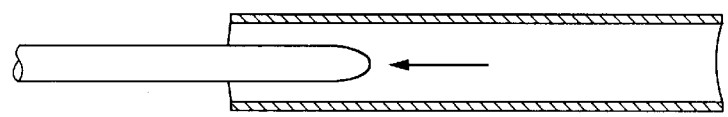
FIG. 12d shows the vessel of a patient with a cannula introduction sheath partially removed from the body vessel.

Another means of increasing the column strength of the device is seen in FIGS. 11(a–c). As seen in FIG. 11c, the wall of the outer tubular elongate body may be made from a stiff, high durometer material having a number of flex points 54 located around the circumference of the body. These points have a considerably thinner wall thickness than the remainder of the body wall 55 and are consequently more readily collapsible if the body is subjected to a contracting force (i.e. an internal vacuum). In the configuration of flex point 54 shown in FIG. 11c, the body will bend inward at the flex points to form a flower shaped cross-section as seen in FIG. 11a. This structure offers an advantage over other designs in that the column strength of the device can be made sufficient to allow insertion of the cannula without reinforcing structures. This eliminates the requirement to use a guidewire or stiffened support without sacrificing the required flexibility necessary to allow insertion of the cannula into the body passage. A guidewire may also be used with this design as well as with the other embodiments disclosed herein to augment the column strength of the device and to aid in the insertion of the device into the vessel.

Figure 4A:
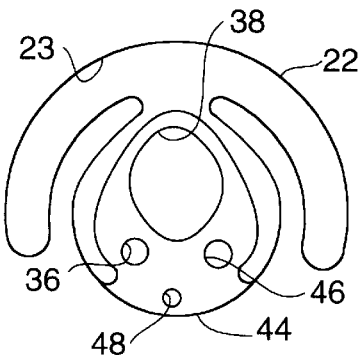
FIG. 4a is a cross-section of one embodiment of the present invention showing an alternative configuration having multiple lumens with the device shown contracted to a first diameter.
Figure 4B:
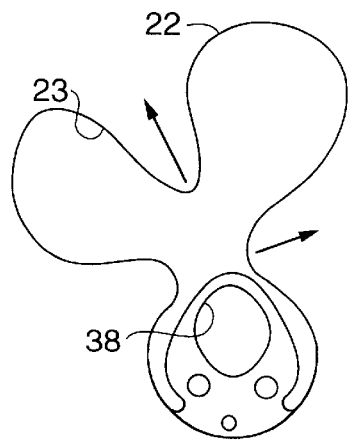
FIG. 4b is a cross-section of one embodiment of the present invention showing an alternative configuration having multiple lumens with the device shown expanding to a second diameter.

Another configuration can be seen in FIG. 4a and FIG. 4b. This is a similar embodiment to that disclosed in FIG. 2 with a different geometry chosen for the tool/cardioplegia lumen 38. FIG. 4a discloses including pressure lumens 48 and 36, inflation lumen 46, main perfusion lumen 23, and tool lumen 38. In general, the largest lumen will be for arterial return while the next largest will be used for cardioplegia. The cardioplegia lumen may also double as a tool lumen, though not at the same time. The smallest lumens may be used for balloon inflation and pressure monitoring. Pressure monitoring at catheter tip, distal to balloon, is most important, and a second lumen could be used to monitor the distal arterial flow pressure, as well. It can be appreciated that a wide variety of geometries and configurations may be chosen with regards to the arrangement, number and relative sizes of the lumens, the design of the inner tubular elongate body and the outer tubular elongate body without departing from the spirit and teachings of the present invention. The main consideration behind the configuration chosen is the desired application for the cannula.

Figure 5:
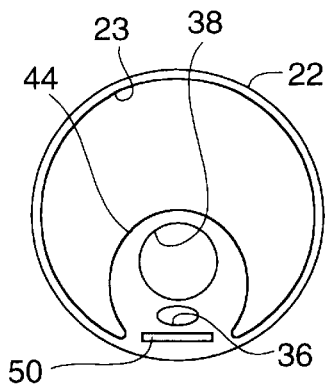
FIG. 5 is a cross-section of one embodiment of the present invention showing an alternative configuration having multiple lumens with the device shown expanded to a second diameter.
Figure 6:
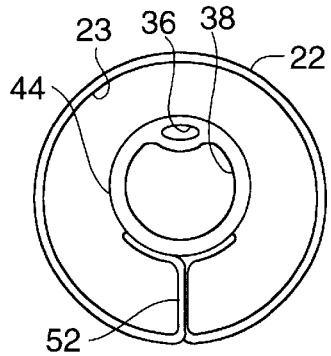
FIG. 6 is a cross-section of one embodiment of the present invention showing an alternative configuration having a centrally disposed inner tubular elongate body with multiple lumens therein.
Figure 8:
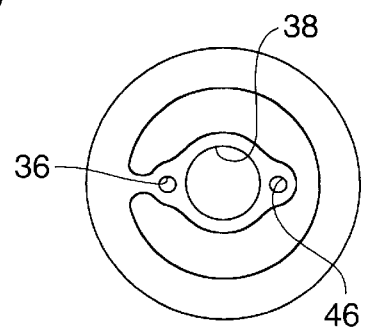
FIG. 8 is a cross-section of one embodiment of the present invention showing an alternative configuration having multiple lumens centrally disposed within the outer tubular elongate body.

An alternate configuration of the cannula can be seen in FIG. 5 wherein the inner tubular elongate body includes a guidewire lumen 50 configured to allow the introduction of a flat metal guidewire to aid in the insertion of the cannula into the vessel. It must be noted that the configuration seen in FIG. 5 may be less desirable because red blood cells tend to collect and clot in small corners and nooks within a cannula. The connection between inner tubular elongate body 44 and outer tubular elongate body 22 creates a narrow channel at that point. A narrow channel should be avoided by using a junction such as seen in FIG. 6 or FIG. 2 to prevent accumulation of blood cells in the channel and subsequent clotting.

Figure 7A:
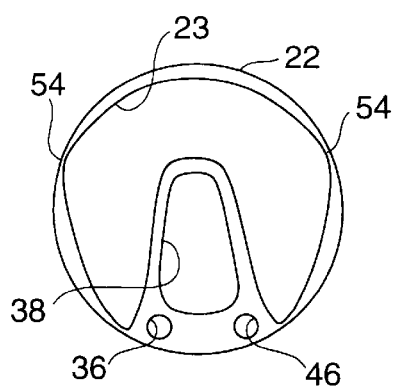
FIG. 7a is a cross-section of one embodiment of the present invention showing an alternative configuration having multiple lumens with the wall of the outer tubular elongate body having thinned wall portions acting as hinge portions for contraction of the outer tubular elongate body.
Figure 7B:
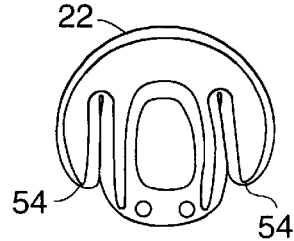
FIG. 7b is the device of FIG. 7a contracted to a first diameter.
Figure 10:
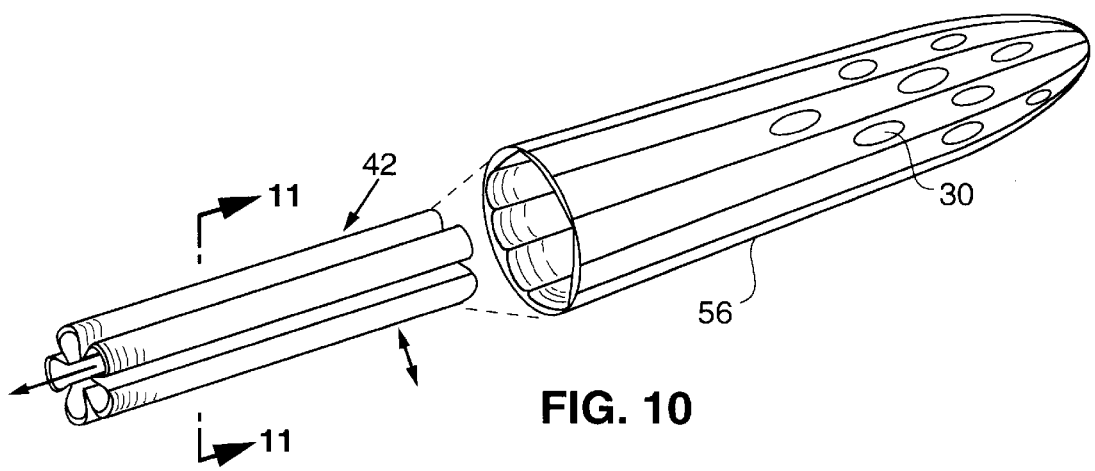
FIG. 10 is a configuration of the present invention using a sheath introducer fitted to the distal end of the expandable cannula.

FIG. 7a shows another preferred embodiment of the present invention. The wall of the outer tubular elongate body 22 is configured in similar fashion to the previously discussed device shown in FIG. 10 and FIGS. 11(a–c). This embodiment is further provided with a inner tubular elongate body 44 with internally formed tool/cardioplegia lumen 38, pressure monitoring lumen 36 and inflation lumen 46. As in other designs, additional lumens may be provided to allow additional functions such as venting or guidewire passage. The relative lumen sizes may also be varied to suit the desired application. The outer tubular elongate body is configured having a number of hinge points 54 with a thinned wall thickness so that the device tends to take the shape shown in FIG. 7b when it is contracted to its first diameter. The device may be maintained in the first diameter either by using a vacuum on the perfusion lumen, disposing the device within an introducer sheath, fastening the device onto itself, or in some similar fashion. The device will be expanded to the second diameter once perfusion flow is desired by releasing the device to return to its natural state using the resilience of the cannula material.

Figure 18:
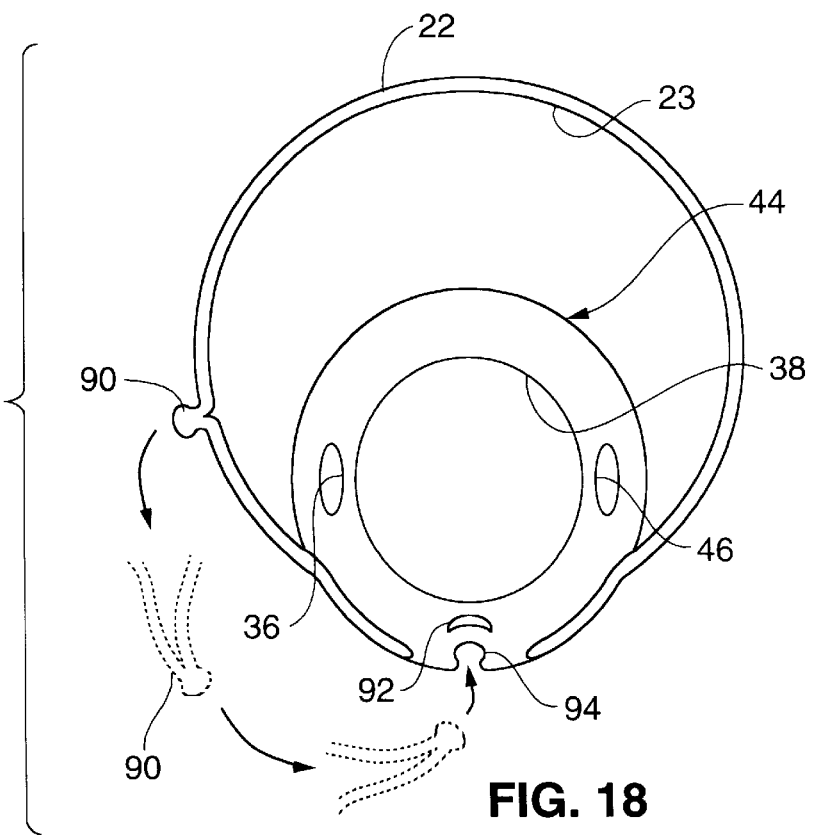
FIG. 18 is a cross-section of an alternative configuration of the present invention having a tongue and groove structure located on the outer tubular elongate body with the device shown expanded to a second diameter.

One means of fastening the device onto itself can be seen with reference to FIG. 18. The outer tubular elongate body 22 is provided with a tongue structure 90 which fits into a corresponding groove structure 94. It is preferred that the groove structure 90 run the entire length of the cannula to eliminate potentially traumatic protuberances on the exterior of the cannula. In this configuration, the tongue 90 is inserted into the groove structure 94 prior to inserting the cannula into the vessel. The device includes a guidewire lumen 92 having a half moon or other functionally specific shape. The guidewire is shaped so that on insertion into the guidewire lumen 92, the guidewire exerts pressure on the groove structure to securely hold the tongue 90 in place within the groove structure 94. When it is desired to expand the device to the second diameter, the guidewire is removed from the lumen 92 and the groove structure 94 expands and releases the tongue 90. Perfusion may then be administered to the vessel using the now expanded perfusion lumen 23.

Another embodiment of the invention can be seen with reference to FIG. 9(a–c). The expandable cannula comprises a woven mesh outer tubular elongate body which compresses radially when exposed to axial expansion and expands radially when compressed axially. The mesh portion 49 is preferably covered with a compliant fluid-impervious material which is provided with one or more perfusion openings at the distal end as in prior designs. As seen in FIG. 9a, the mesh portion 49 may be introduced into the access site through the vessel wall 33 via an introducer sheath 47. This sheath is advanced to the area of interest and the mesh portion 37 is then deployed from the distal end of the introducer sheath into the vessel lumen and allowed to return to an unstretched, axially expanded condition. The outer tubular elongate body is continuously fed through the introducer sheath 47 until the expandable cannula is in place in the vessel to be perfused. The cannula of FIG. 9a further includes a inner tubular elongate body 44 having one or more lumens therein and an expandable member 24 located near the distal end of the inner tubular elongate body 44.

An alternative embodiment of the expandable braided mesh cannula can be seen with reference to FIGS. 9(b–c). The cannula 42 is introduced into the target vessel via a percutaneous incision or a direct cut-down procedure as explained in detail below. In order to facilitate the insertion of the cannula and prevent trauma to the interior of the vessel, the cannula is contracted by axially stretching the braided mesh sheath 37. This can be accomplished by manually pulling the proximal end of the sheath 121. Fitting 120 is provided on the proximal end 121 for connection to a supply of arterial return. The inner tubular elongate body 44 is configured having a number of lumen integrally formed within, including a pressure lumen 48, an inflation lumen 46, and a multi-function lumen 36. These lumens are provided with fittings 132, 128, and 130 at the proximal ends, respectively. A guidewire 27 may also be used for insertion of the cannula into the target vessel.

FIG. 9c shows the braided mesh sheath 37 in a fully expanded condition. This can be done by releasing the axial tension on the proximal end 121 of the cannula and allowing the sheath 37 to return to a relaxed second diameter. Perfusion flow may be provided in the expanded sheath 37 through the arterial return apertures 30 provided in the distal end of the sheath, or at other specific locations along its length. As in other embodiments, an expandable member 24 may be fixed at the distal end of the inner tubular elongate body 44. Preferred materials for construction of the braided sheath include polyester monofilaments such as Dacron. The sheath 37 may be coated with an impermeable, flexible membrane such as silicone or polyurethane.

Figure 13A:
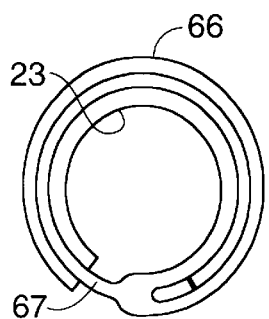
FIG. 13a is a cross-section of an expandable cannula showing an alternative configuration of the cannula shown contracted to a first diameter.
Figure 13B:
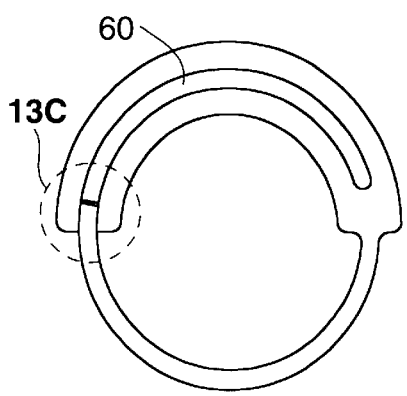
FIG. 13b is a cross-section of the device of FIG. 13a with the outer tubular elongate body expanded to a second diameter.
Figure 13C:
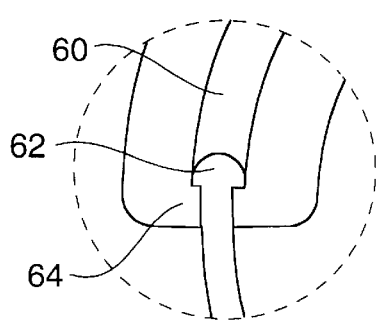

One embodiment of an expandable cannula can be seen with reference to FIG. 13(a–b). The cannula has an outer tubular elongate body having a double walled portion 66 and a single walled portion 67. The single-walled portion and the double walled portion each have a free end and are joined relative to each other so as to form a single unitary body having a substantially circular cross-section. The single walled portion 67 is receivable in the recess 60 between the first and second walls of the double walled portion 66. During contraction, the single walled portion is almost completely disposed within the recess 60. The single wall is slidingly engaged in the recess and slides outward when the cannula is expanded to the second diameter as shown in FIG. 13b. When the cannula is completely expanded, only a small portion of the single walled portion 67 is engaged in the recess 60. A stop 62 may also be provided at the free end of the single walled portion 67 to prevent the single walled portion from being completely removed from the recess 60 during expansion of the cannula. The stop 62 is prevented from passing beyond a narrowed portion 64 provided at the free end of the double walled portion 66. In operation, creating a fluid seal between the single walled portion 67 and the recess 60 may prove difficult. However, this is not a critical problem as a minor amount of leakage into the vessel will merely join the other arterial return flow that is perfused into the vessel.

Figure 14A:
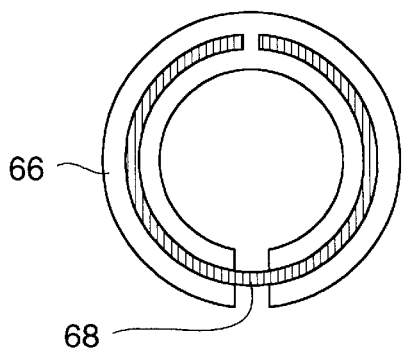
FIG. 14a is a cross-section of an expandable cannula cannula with the device shown contracted to a first diameter.
Figure 14B:
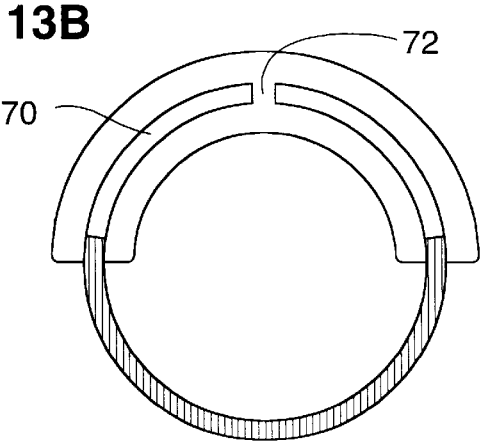
FIG. 14b is a cross-section of an expandable cannula with the device shown expanded to a second diameter.

FIG. 14(a–b) shows an alternate configuration wherein the single walled portion 68 and the double walled portion 66 are separate structures. As in the prior device, the single walled portion 68 has an arcuate cross-section with the double walled portion 66 similarly shaped. The free ends of the single walled portion 68 are inserted into a pair of recesses 70 between the first and second walls of the double walled portion 66. The single walled portion 68 is slidingly disposed within the recess so that the single walled portion 68 is almost fully disposed within the recess when the device is contracted to a first diameter. The single walled portion 68 is only partially disposed within the recess 60 when the device is expanded to the second diameter. As before, a stop (not shown) may cooperate with a narrowed portion of the recess 60 to prevent the single walled portion 68 from becoming disengaged from the double walled portion 66.

Figure 15A:
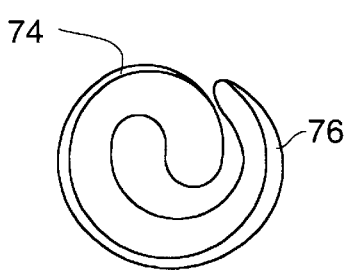
FIG. 15a is a cross-section of configuration of the present invention shown contracted to a first diameter.
Figure 15B:
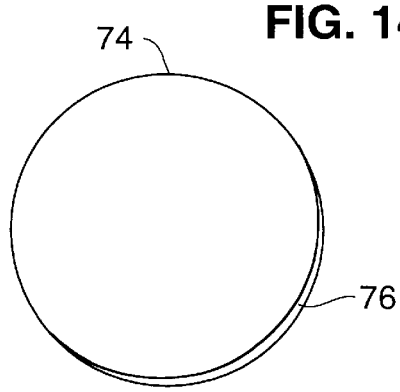
FIG. 15b is a cross-section of a configuration of the present invention with the device shown expanded to a second diameter.

Another embodiment of an expandable cannula is seen at FIG. 15a. The wall of the tubular elongate body is configured having a thin walled portion 74 and a thick walled portion 76 which define an unbroken circular cross-section. Unlike the devices shown in FIGS. 13 and 14, there is no potential leakage from the cannula from the engagement of the two walls. The thin-walled portion 74 is configured to be more flexible and compliant than the thick walled portion 76. When the device is contracted to the first diameter, the thin-walled portion 74 folds in on itself and the thick walled portion 76 is configured to dispose itself around the folded thin-walled portion 74, forming a substantially circular cross-sectional configuration as shown in FIG. 15a. The configuration shown in FIG. 15a offers a reduced diameter configuration with sufficient column strength to allow endovascular insertion of the device into the body vessel.

Figure 16A:
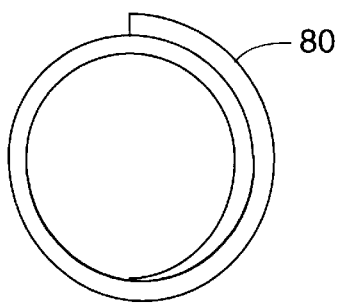
FIG. 16a is a cross-section of a configuration of the present invention with the device shown contracted to a first diameter.
Figure 16B:
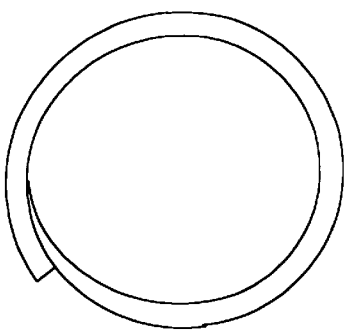
FIG. 16b is a cross-section of a configuration of the present invention with the device shown expanded to a second diameter.

FIG. 16(a–c) shows another configuration wherein the outer tubular elongate body is formed of a single strip 80 of flexible material that has been coiled into a circular configuration. Coiling and uncoiling of the strip 80 causes the device to expand and contract from the first diameter to a second diameter. As strip 80 uncoils, the amount of overlap between the inner and outer edges decreases. As seen in FIG. 16*c* one of the edges may be scalloped, castellated or otherwise notched. As the second diameter is approached, these notches are revealed, allowing escape of blood while preventing further expansion of the cannula.

Figure 17A:
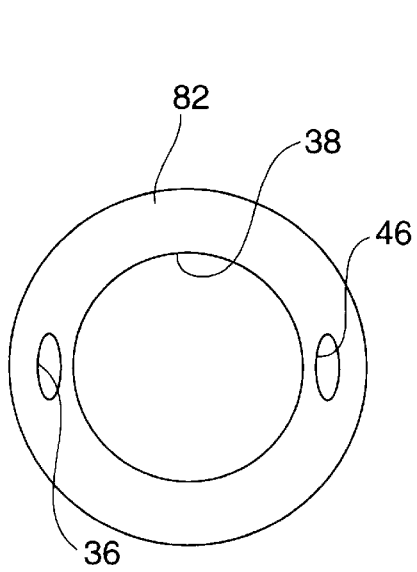
FIG. 17a is a cross-section of a configuration of the present invention with the device shown having an unexpanded first diameter.
Figure 17B:
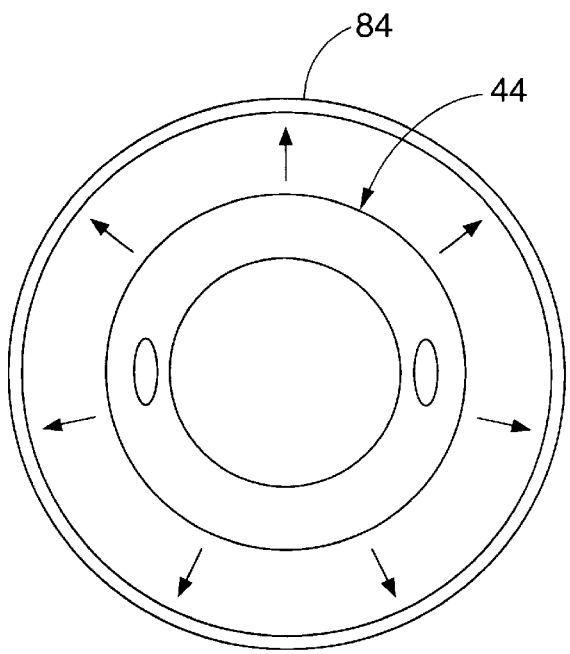
FIG. 17b is a cross-section of a configuration of the present invention with the device shown expanded to a second diameter.

Yet another embodiment of an expandable cannula is seen at FIG. 17(*a–b*). The outer tubular elongate body 84 that transports the arterial return blood is formed from and becomes distinct from the inner tubular elongate body 44 by causing delamination of the outer tubular elongate body 84 from the inner tubular elongate body 44. The delamination of tubular body 82 into an inner tubular elongate body 44 an outer tubular elongate body 84 occurs as fluid (i.e. arterial return blood) is forced between the layers at the proximal end of the cannula. As fluid is forced in, the delamination proceeds to the distal end of the cannula. The cannula is preferably composed of an irradiated, cross-linked polymer that, when expanded as in the outer tubular layer 84, expands easily to a set diameter and becomes non-elastic beyond that diameter.

It can be seen that the device of the present invention can be manufactured in a manner similar to traditional cannula systems. However, the devices described in the foregoing embodiments offer a number of advantages over prior devices. It is highly desirable to have a cannula which can perform multiple functions. However, such a cannula is limited in size as it must be readily insertable into the body vessel. Larger cannulae can increase the risk of trauma to the vessel walls and dislodge embolic debris into the blood stream. The teachings of the present invention disclose a multi-functional cannula having a cross-sectional silhouette which is smaller than many single function cannulae.

Cannulae constructed using traditional techniques have diameters in the range of 9–11 French for a dual or triple function cannula designed to occlude the aorta of the patient and provide cardioplegia flow to the aortic root and coronary arteries and/or monitor aortic root pressure. Multi-lumen cannulae that are designed to deliver arterial return blood as well as the above-mentioned functions, are typically around 21 French in diameter. The present invention can be configured to have a first diameter of 15 French (0.5 cm) when inserted which can be expanded to 24 (0.8 cm) French for delivery of perfusion flow. Thus, while in a typical patient, the ascending aorta has a diameter of approximately 3 cm., the present invention can be easily threaded into the aorta because the aorta has a diameter 6 times greater than the inserted cannula, however, a specific area of concern during endovascular insertion of the cannula is the femoral artery. A catheter having an outside diameter 21 to 24 French will occlude this artery. A key aspect of the present invention is the capability to offer a cannula diameter that is less than 18 French upon insertion while offering multiple function capabilities.

The present invention is also not limited to arterial or venous access via an endovascular insertion into the femoral artery or the femoral vein. Femoral access was traditionally viewed as the most desirable access method because of the lumen diameter requirements for insertion of traditional devices. However, because of the reduced size of the cannula on insertion, and the increased flow possible through the perfusion lumen, the present invention may be used to access vessels with smaller lumens, most particularly the left subclavian artery. The left subclavian artery provides almost direct access to the aortic arch while avoiding the curved path from the femoral access site to the region of interest. Subclavian access is also more desirable because the scaling and other debris that is dislodged in either subclavian will not likely travel to the brain of the patient, where the most serious embolisms occur.

The present invention can also be used to access both the venous and arterial system of the patient via other alternative sites besides the subclavian arteries and/or brachiocephalic trunk. Access via an abdominal aorta incision, a direct aortic arch stick via an endoscopic trocar, a minimally invasive para-sternotomy or mini-sternotomy or thoracotomy, a central access full sternotomy, or an approach through either atrium and through the mitral and aortic valves are other applications wherein the expandable cannula of the present invention provides an improved means of providing CPB functions to the venous and arterial system of the patient.

The device of the present invention is well suited for application to the venous system of the patient. During CPB, a cannula of the present invention can be inserted into the left or right femoral vein and inserted into the vein of the patient to access the patient's venous system through the right side of the heart (typically the right atrium), or directly through the superior vena cava (SVC) and/or inferior vena cava IVC, or through a peripheral vein access sites. The device may also be inserted into the internal jugular vein of the patient and advanced to the right atrium, the SVC and/or IVC, or the pulmonary artery, to withdraw blood therefrom. Once that the device has been inserted in its first diameter to the venous region of interest, the device is expanded to the second diameter and used to drain deoxygenated blood from the venous system. The cannula can remain expanded until the completion of the procedure at which time it may either be removed while maintaining it in a second diameter or it may be contracted to first diameter and removed.

The construction of a venous drainage cannula capable of expansion from first to a second diameter is similar to the construction of an arterial cannula as described herein except that the device is configured to remove blood from the venous system of the patient instead of providing fluid flow to the arterial system. For this reason, an expandable cannula suited for application to the venous system of the patient is configured having an open distal end which functions as a drainage port through which blood is removed from the venous system to an external CPB machine. The venous drainage expandable cannula may also include and expandable member located at the distal end of the cannula proximal to the drainage port wherein the expandable member is configured to maintain the cannula in the region of interest during the drainage of the blood from the venous system of the patient. The insertion of a venous drainage expandable cannula is also similar to the insertion of an arterial expandable cannula as herein described except that the access site chosen provides access to the venous system of the patient, e.g. the internal or inner jugular veins, the right and left subclavian veins, or the left and right femoral veins.

The method of use of the previously described devices are similar to the methods used for the endovascular insertion of traditional cannulae. To use the device of the present invention for a CPB procedure wherein the cannula is inserted via a "cut-down" or percutaneous incision in the femoral artery for perfusion of the arterial system of the patient with oxygenated blood from an external CPB machine, an access site must first be prepared in the right or left femoral artery of the patient.

A percutaneous access site is prepared in the following manner. A solid piercing needle, disposed within a thin walled metal sheath that allows the needle tip to protrude, is inserted through the patient's skin and into the femoral artery, angled so that tip is cephalic. The needle is removed, leaving the needle sheath lumen open for the guidewire. A short introducer guidewire is quickly (to reduce blood loss) inserted through the needle sheath. The needle sheath is removed over the guidewire and then a plastic, sheathed vessel dilator is threaded over the short guidewire, the vessel dilator having a tapered tip which is pushed into the femoral artery, creating a larger opening in the vessel. The short introduction guidewire is removed and replaced with a long specialized guidewire. The guidewire is then positioned over the aortic arch to guide the endovascularly inserted cannula. The vessel dilator is removed over the guidewire, leaving the plastic introducer sheath penetrating the vessel wall with the guidewire positioned within the aortic arch. The sheath has a hemostasis valve at the proximal end that seals against blood flow while allowing passage of instruments such as a guidewire, dilator, or the expandable cannula.

The preferred access method to the femoral artery for a cannula of the size of the present invention is to use a direct "cut-down" procedure. A percutaneous access site would tend to tear the surrounding tissue because of the small size of the initial puncture. For femoral access, the cut-down is made through the patient's leg flesh to the femoral artery. The femoral artery is dissected away from surrounding tissue for a short distance to expose it for ease of access and a ⅛ inch wide cloth tape or ribbon may be placed around the backside of the artery. A small longitudinal incision is made proximate an artery of sufficient depth to provide access to the artery for immediate placement of the dilator and sheath. Direct proximal occlusion by the surgeon's finger, an instrument, or the cloth strip around the vessel may be utilized by the surgeon before insertion until the dilator is placed and the cloth tape is tightened around the dilator sheath. A plastic, sheathed vessel dilator similar to that used in the percutaneous approach is threaded over the short guidewire with its tapered tip pushed into the femoral artery, creating a larger opening in the vessel. A long, specially-shaped guidewire is inserted through the dilator and is positioned over the aortic arch to guide the expandable cannula. The vessel dilator is removed over guidewire, leaving the plastic introducer sheath penetrating the vessel wall with the guidewire positioned within the vessel. The sheath has a hemostasis valve (one of several types) at the proximal end that seals against blood flow while allowing passage of instruments such as the guidewire, dilator, or cannula.

It is important to note that the dilator sheath must have sufficient resilience to allow the device of the present invention to be inserted and expanded in the area of the port. Sheaths having sufficient dilation qualities are well known in the art and are readily available for this application.

Following preparation of the access site, the cannula must be readied for entry into the femoral artery. An important consideration when inserting any cannula into the body is to ensure that the cannula is completely devoid of air. Beginning perfusion flow with air pockets contained in the expandable cannula will result in an "air emboli," a potentially life threatening occurrence. Therefore, the cannula must first be completely purged of air by filling the expandable cannula with saline or other biocompatible fluid prior to insertion of the cannula to prevent gas bubbles in the blood. A number of well known techniques are available in the art for removing the air from a body, any of which would be suited for this application.

Figure 23:
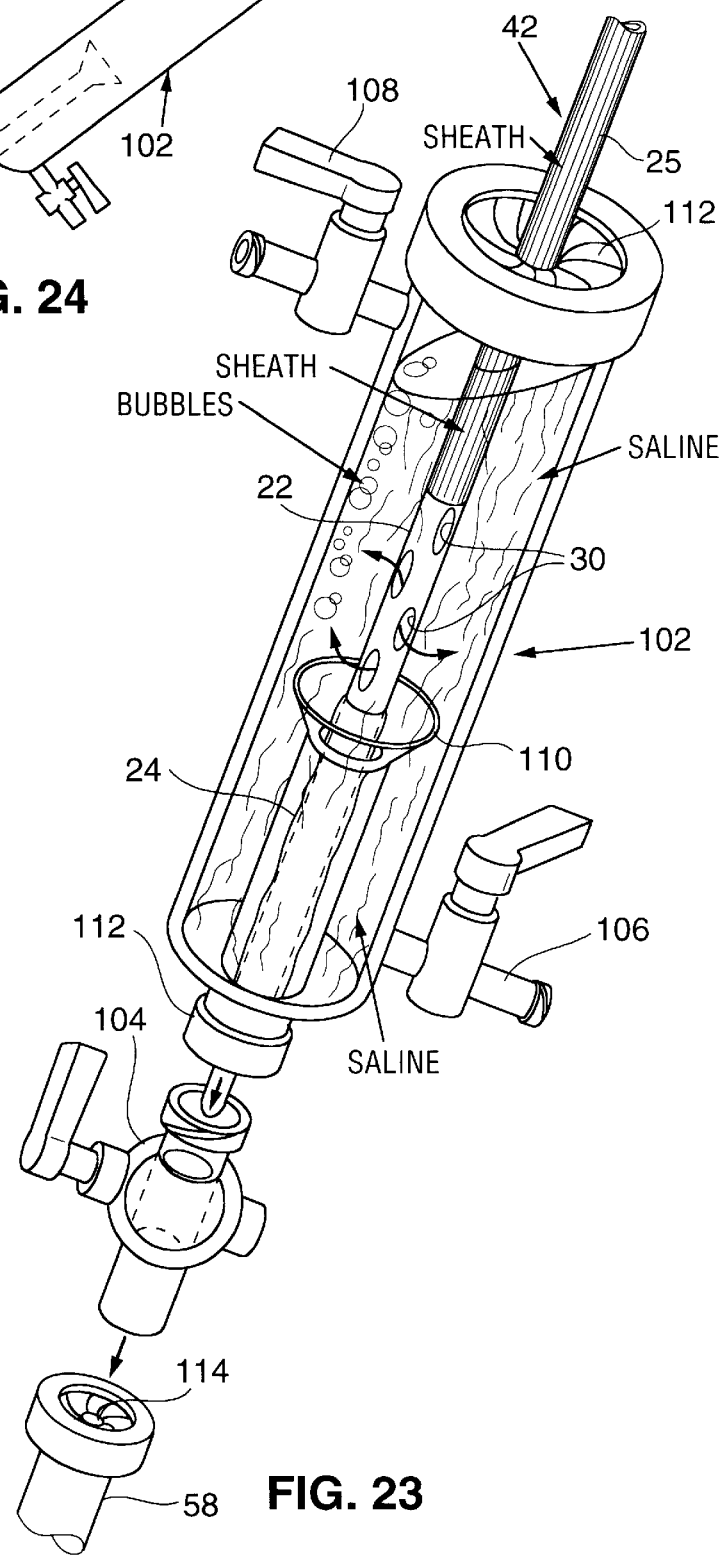
FIG. 23 is a device used to remove air pockets from the cannula of the present invention shown with the cannula in place within the device.

One method for removing the air from a cannula will be described with reference to the attached drawings. In FIG. 23, a sheathed cannula 42 is shown inserted into a saline filled bubble-trap 102. The proximal end of the perfusion lumen of the cannula is connected to a saline-filled syringe (not shown). The sheath 25 on the cannula 42 initially extends distally to the cannula tip 21, holding both the occlusion balloon 24 and the outer expandable tubular elongate body 22 in the smallest possible cross-sectional configuration.

The bubble trap 102 is a transparent, plastic, saline-filled cylindrical container with an overflow vent 108, drain fitting 106 and portal tips 112 at both ends. It has a detachable tubular distal tip 104 (with a hollow-bore spherical valve to allow cannula passage) used to engage hemostasis valve 114 on introducer sheath 58, and an internal extension 110 of that tip that acts as a sheath for the cannula tip 21 when the sheath 25 is partly retracted. The proximal end of the internal extension 110 includes a large open port that accepts the sheathed cannula 42.

The fully sheathed cannula 42 is inserted so that it is submerged to greater depth than the arterial return apertures 30 located just proximal to the occluding balloon 24. During insertion, the occluding balloon portion 24 is visibly guided into the internal tip extension 110 previously mentioned. As seen in FIG. 23, the sheath 25 is retracted manually at the proximal end, exposing the occluding balloon 24 and distal arterial return apertures 30 on the cannula. The balloon remains in a small collapsed state as it is still contained by the internal tip extension 110.

The saline-filled syringe that is connected to the proximal end of the arterial lumen is now slowly emptied into the cannula. Since the sheath 25 still contains the expandable perfusion lumen in a collapsed state, the saline travels quickly through the small internal space remaining, purging all air from the lumen without expanding it. The distal end of the bubble-trap 102 is observed to demonstrate complete purging. Air escapes out the vent 108. The bubble-trap/cannula/syringe assembly can now be inserted into the hemostasis valve 114 on the introducer sheath 58 installed as described above.

The hollow-bore spherical valve 104 on the tip of the bubble-trap is now opened, allowing blood, under patient's blood pressure, to momentarily back-flow into the bubble trap, purging any air in the tip proximity. The cannula 42 is immediately inserted a short distance through the bubble-trap tip into the introducer sheath 58, effectively sealing against significant blood loss when the bubble-trap is removed. The bubble trap 102 is drained or aspirated with a syringe (not shown) via the drain fitting 106 and the syringe on the proximal end of cannula is removed, momentarily allowing blood to push some saline back out, while the bubble-trap 102 is removed so that no air enters the cannula 42. The bubble-trap is disconnected from the hollow-bore spherical valve 104 and slid back off of the proximal end of the cannula 42 without pulling the cannula back with it. Spherical valve 104 remains unobtrusively engaged to introducer sheath 58, with cannula passing therethrough.

The sheath 25 over the cannula 42 can now be completely withdrawn back out over the proximal end of the cannula 42 and discarded, allowing the outer expandable tubular elongate body 22 on the cannula 42 to be inflated with arterial blood or expanded in some other manner herein described. This step may be done also after the final positioning step if a peel-away sheath design is used. The arterial return blood tubing (not shown), which is cross-clamped until appropriate time, is connected to the cannula 42 at the proximal end.

In order to aid in the insertion of the device, the diameter of the cannula 42 is at its smallest configuration for insertion into the introducer sheath 58. As described above, the cannula 42 may be maintained in its first diameter by using a sheath 25 as seen in FIG. 23. The reduced cannula diameter can also be maintained by using an external vacuum. This is accomplished by connecting a vacuum source to the proximal end of the perfusion lumen. As described more specifically in the embodiments above, the device is configured so that this vacuum will cause the outer tubular elongate body to reduce in overall diameter. Because the outer tubular elongate body is configured with one or more arterial return apertures 30 located at or near the distal end of the cannula 42, the cannula 42 must be configured to allow a vacuum to be maintained in the perfusion lumen 23. This can be accomplished by installing a one way valve in the perfusion aperture which will only allow fluid flow out of the lumen 23 and will close if the pressure in the lumen 23 drops below the pressure in the aorta. A vacuum may also be maintained if the outer tubular elongate body 22 is configured to be compliant enough so that a seal is formed by the tubular elongate body folding in on itself.

Another method of contraction that is contemplated by the present invention is to configure the cannula so that the natural state of the cannula is to remain in the first diameter. The materials of the cannula are such that the device will be expanded to a second diameter when the perfusion flow is provided to the perfusion lumen of the cannula. The material will be sufficiently compliant that the relatively low pressure at which the perfusion flow is provided will be sufficient to expand the cannula to the second diameter. A preferred material for this embodiment would be an irradiated polyethylene that is relatively non-elastic and retains a memory of its folded position.

A superior feature of the present invention over the prior art is that the device may be inserted into the vasculature of the patient to a region of interest while in a first, unexpanded diameter and then expanded to a second, expanded diameter when it is desired to provide CPB functions at the region of interest. It is thus possible to provide a cannula which has a smaller diameter at insertion than any available prior device so as to minimize patient trauma during insertion of the device while maximizing the availability of access sites, yet can be expanded to have a functional diameter greater than available with prior devices so as to maximize the potential applications and possible functions which may be provided to the region of interest.

In particular, a device can be constructed which may be inserted having a diameter in the range of 6–21 French on insertion. The specific configuration of the device will depend on the functions that are desired to be provided by the cannula. For a two lumen cannula having a first lumen for inflation of an expandable member and a second lumen for providing arterial return flow or other fluids to the body passageway, the expandable cannula may be constructed to have a first diameter between 6 and 10 French. For an expandable cannula including a third lumen which may be used for tool access, cardioplegia, venting, or other CPB functions, the cannula will have a first diameter between 8 and 14 French. Including a fourth lumen for pressure monitoring or other functions will increase the first diameter of the device to between 10 and 21 French. A preferred embodiment of the device will have a four lumen design with a first diameter of 13 to 15 French. Upon insertion, the device will be expandable to a second diameter of 22 to 26 French.

The expanded second diameter of the device will generally vary with the functions that are to be provided with the cannula. In order to provide arterial return functions to the ascending aorta, a perfusion lumen having a 19 to 26 French lumen will generally be required. The maximum diameter of the device will also depend on the desired point of entry into the vasculature of the patient and the individual characteristics of the patient. The subclavian arteries of a patient may range between 12 to 30 French depending on the size and condition of the patient. Likewise, the femoral arteries vary between 24 and 36 French. A maximum outer diameter of between 21 and 30 French is suited for many applications and access sites.

Figure 19:
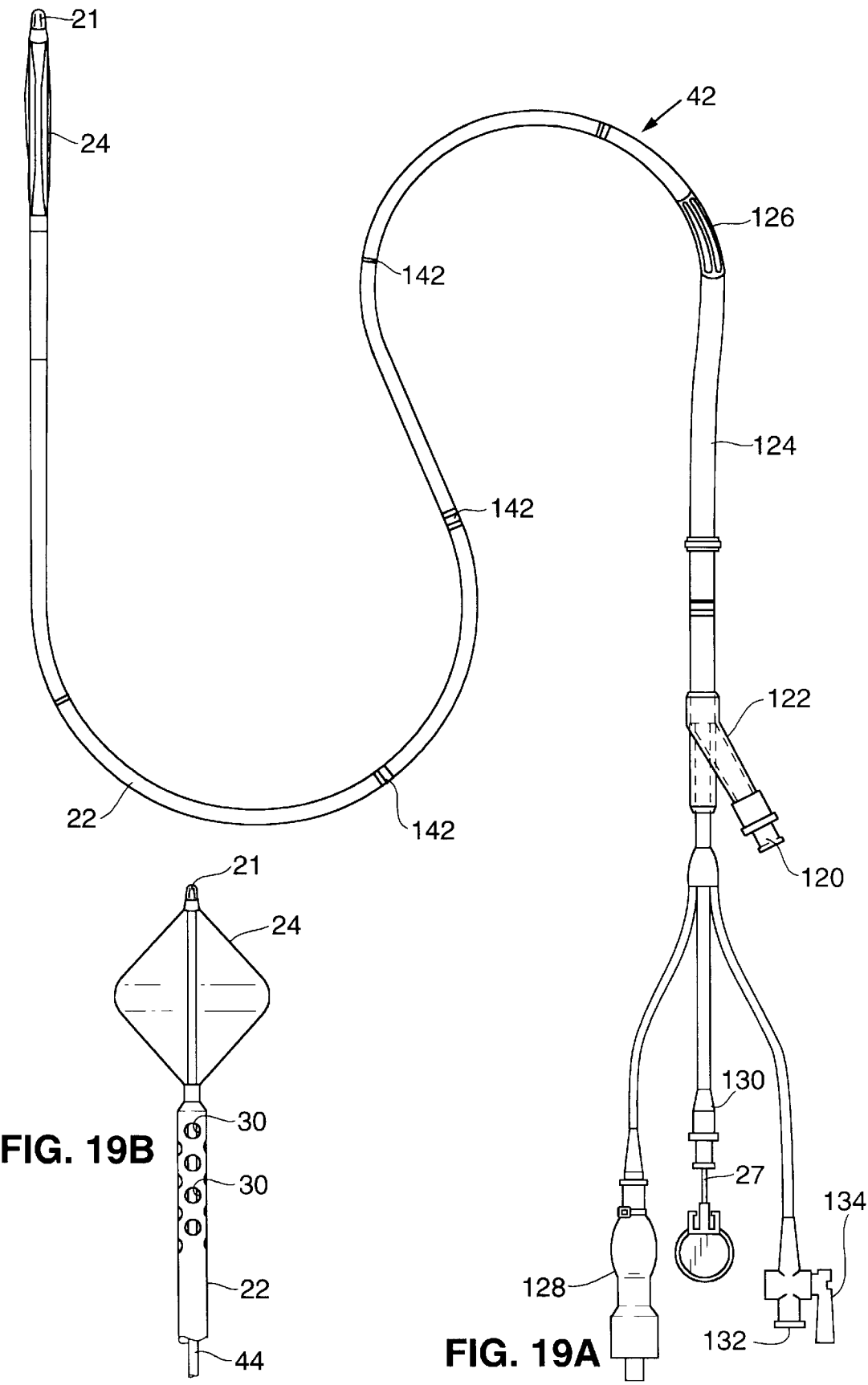
FIG. 19a is of a cannula of the present invention configured to be inserted into the femoral artery of the patient.
FIG. 19b is detail of the distal end of the cannula shown with the expandable member and expandable outer tubular elongate body fully expanded.

FIG. 19(a, b) shows a cannula 42 constructed in accordance with the present invention which is configured to be inserted into the femoral artery of the patient. The cannula is comprised of an expandable outer tubular elongate body 22. The outer tubular elongate body is preferably constructed from irradiated polyethylene, PET or polyurethane film stock having a wall thickness of around 0.015 in. The cross section of the cannula 42 in its expanded state can be seen with reference to FIG. 20 wherein the perfusion lumen 23 is shown fully expanded with an outer diameter of around 26 French and a wall thickness of about 0.015 in. The expandable member 24 is configured to extend 75 to 80 cm into the aorta from the femoral artery and terminate in the ascending aorta. The distal end of the expandable tubular elongate body 22 terminates in a plurality of arterial return apertures 30 as previously described. FIG. 19b shows the distal end of the cannula 42 with the cannula fully expanded and the expandable member 24 inflated to occlude the vessel. Blood enters the expandable tubular elongate body through a luer lock 120 or other connection means integrated into a co-axial "Y" fitting 122 provided at the proximal end of the cannula 42. The blood travels to the distal end of the expandable outer tubular elongate body 22 through the perfusion lumen 23 and passes into the lumen of the aorta through the arterial return apertures 30 which may vary in number, spacing and placement from distal end. The cannula is also provided with a plurality of blood ports 126 distal to a non-expanding cannula portion 124. Ports 126 are located inside the expandable portion 22 where the expandable portion proximally joins the distal end of portion 124. The blood flows out of portion 124 through ports 12b and into lumen 23 inside tubular elongate body 22.

Figure 20:
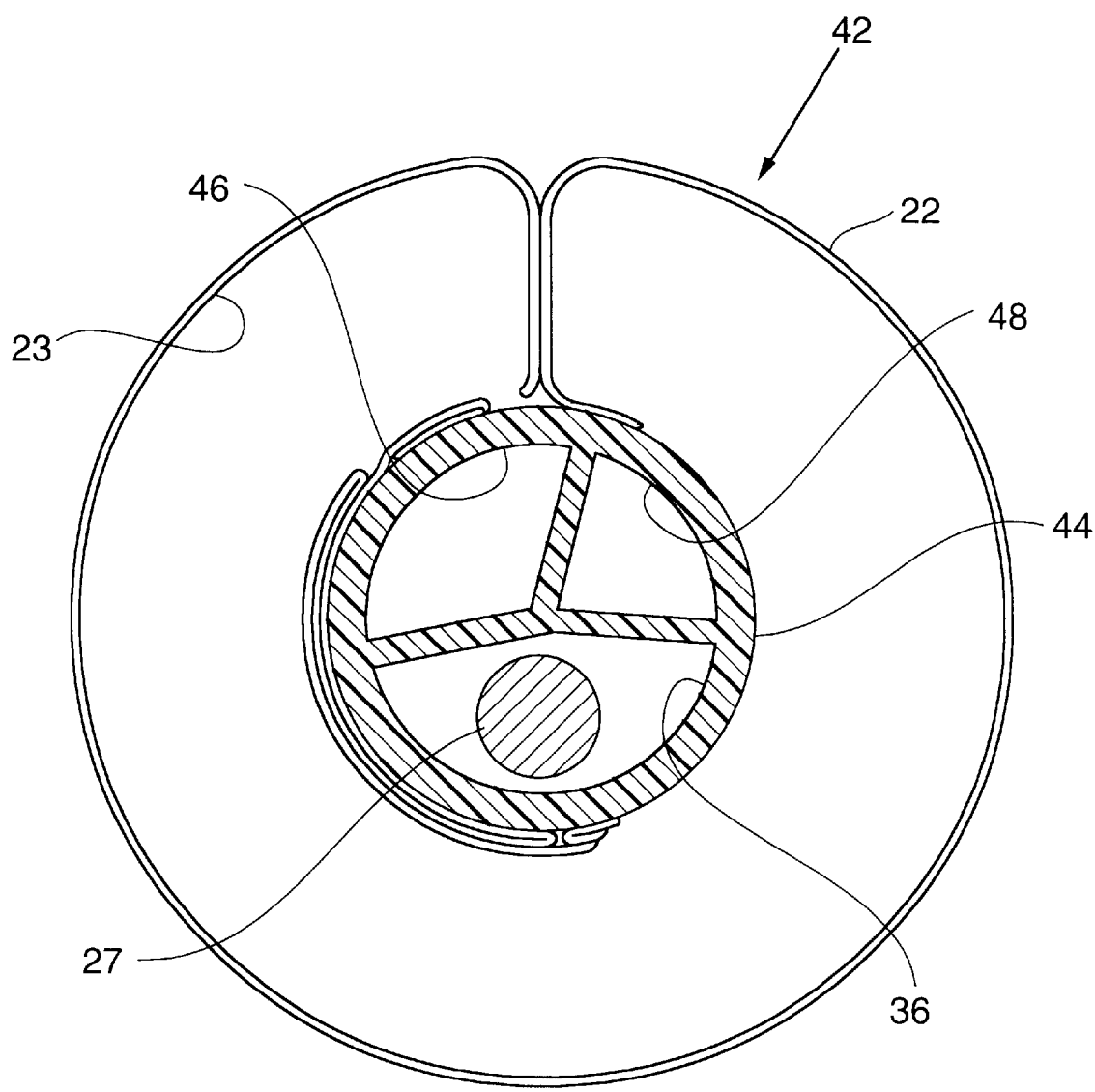
FIG. 20 is a cross section of the cannula showing the inner tubular elongate body and the lumens therein and the outer expandable tubular elongate body in a fully expanded configuration.
Figure 21:
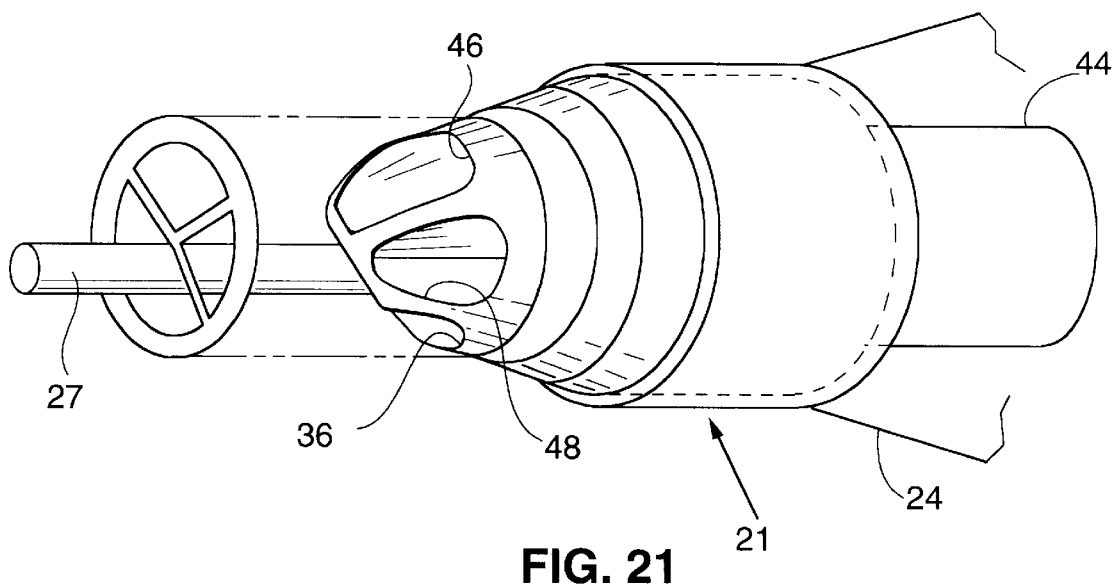
FIG. 21 is of the distal end of the cannula of FIG. 19a showing the integrally formed lumens therein and the configuration of the distal tip of the cannula.

The cannula 42 includes an inner tubular elongate body 44 having three internally disposed lumens, best seen in FIG. 20, including a saline inflation lumen 46, a pressure lumen 48, and a multi-function lumen 36. The multi-function lumen 36 can be used for cardioplegia, venting, insertion of a guidewire 27, or other surgical tool or imaging device. The proximal end of the internally disposed inflation lumen 46 is preferably attached to a standard balloon inflation fitting 128 for a syringe having saline solution therein. The multi-function lumen 36 is preferably provided with a universal fitting 130 at the distal end which can accommodate either an external cardioplegia source (not shown), an inserted guidewire 27 or tool, or a vacuum venting source (not shown). The pressure lumen 48 is configured at the proximal end with a standard pressure monitor luer port 132 with an opening and closing valve 134. The inner tubular elongate body 44 is preferably made from extruded pellothane polyurethane.

Figure 22:
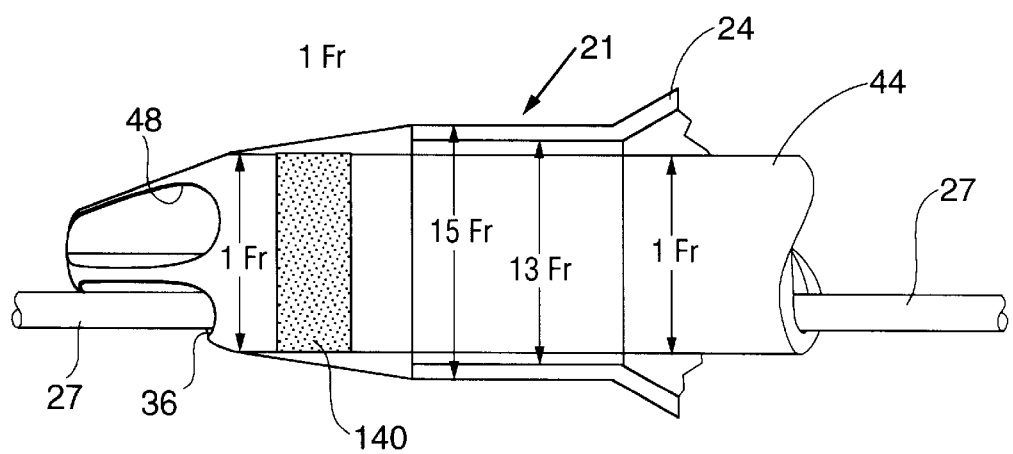
FIG. 22 is of the distal tip of the cannula of FIG. 21 showing the configuration of the tip.
Figure 24:
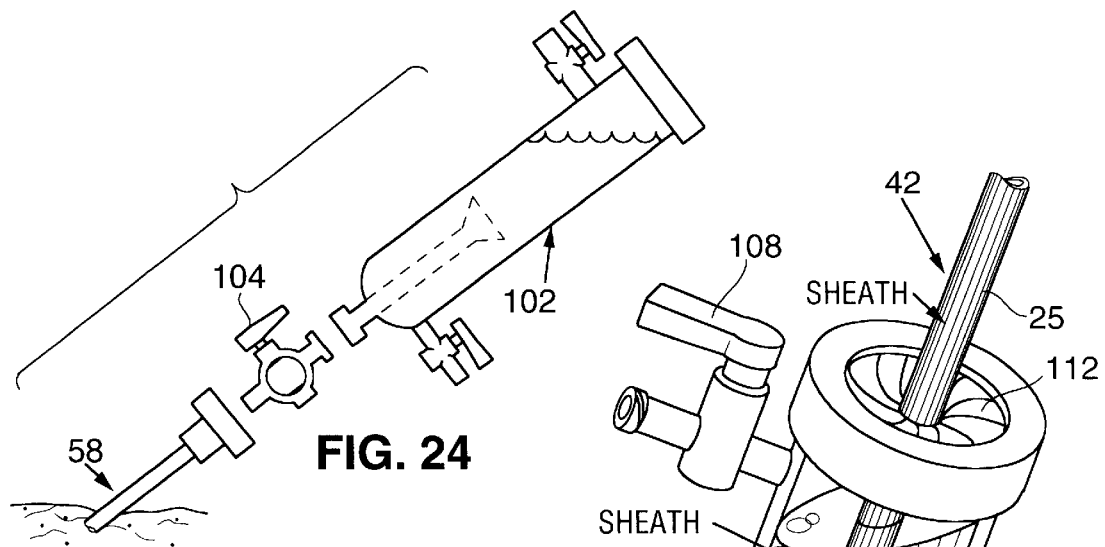
FIG. 24 is the device of FIG. 23 shown detached from an introducer sheath installed in the body vessel of a patient.

The inner tubular elongate body 44 extends distally of the distal end of the outer tubular elongate body 22 and terminates in a distal tip 21. The distal tip, as seen in FIG. 22, can be configured with a radiopaque ring 140 for ready fluoroscopic identification and guidance. The tip is preferably rounded and can be further provided with an atraumatic tip to prevent damage to the vessel lumen during insertion or use. The inflation lumen 46 is fitted with a plug (not shown) at the distal with an inflation outlet (not shown) in fluid communication with the expandable member 24. The distal tip 21 is configured having an outer diameter of between 10–13 French. Located just proximal of the distal tip of the cannula is the expandable member 24 constructed as discussed infra.

With the outer tubular elongate body 22 and expandable member 24 of the cannula configured in a first diameter, the assembly is inserted into the port previously installed in the percutaneous incision or direct cut-down made in the groin upper inner thigh area of the patient and advanced to a point where the expandable member 24 is disposed in the aortic arch just upstream of the brachiocephalic trunk.

A number of methods may be used to thread the device to the point of interest. As previously discussed, an introduction sheath may be used to advance the contracted cannula to the point of interest. As can be seen in FIG. 20, the device of the present invention may be configured having a multi-function lumen 36 provided within the cannula for introduction of a guide wire 27. The lumen can be configured to accept a number of different commercially available guide wires, including steerable guidewires, and guidewires specially shaped for passage through the aortic arch. Once that the cannula is in place in the aorta, the guidewire may be removed for the remainder of the surgical procedure and the lumen 36 may be used to provide access to the aorta lumen for other devices and functions (e.g. insertion of a fiber-optic light camera, delivery of cardioplegia fluid or venting of the aorta lumen).

During insertion of the cannula, fluoroscopic guidance is preferably used to correctly position the cannula within the aorta. For this purpose, radiographic markers 140 are placed on the distal end 21 of the cannula to aid in the imaging of the device. Transoesophageal echocardiography may also be used as an alternate means of imaging the device to insure correct placement within the aorta. Radiographic gradation markings 142 may also be provided on the exterior of the outer tubular elongate body of the expandable cannula so that the operator may readily determine the extent to which the device has been inserted into the vessel.

Using a device as shown in FIG. 19a, when the device is properly inserted, the expandable member 24 is expanded to make secure contact with the interior of the aorta wall. The member need only be expanded to a point sufficient to substantially occlude the lumen of the aorta and prevent migration. Overexpansion of the balloon must be avoided as this may result in a rupturing or damaging of the aortic wall. A balloon diameter of around 3.5 cm and expansion pressure of about 250–350 mm Hg has been shown effective for this application.

The expandable member 24 may be an inflatable balloon made from such materials as polyethylene terephthalate (PET), polyvinyl chloride (PVC), ethylene vinyl acetate (EVA), silicon, latex, or some other such material. An inflation lumen 46 is used to inflate the member and occlude the aorta. The expandable member may also be comprised of a low density foam about which is disposed a substantially fluid impermeable member. The member is subjected to a vacuum through the inflation lumen 46 to maintain the member in a collapsed state. When the vacuum is released, the resilience of the foam causes the balloon to expand and occlude the aorta. The expandable member is configured having an inner surface and an outer surface whereby on expansion of the member, the outer surface of the expandable member is expanded to contact an interior wall of the body passageway into which the expandable cannula is inserted. For aortic occlusion, the outer surface of the expandable member contacts the interior wall of the aorta so as to occlude the aorta.

Once the aorta 20 is substantially occluded, delivery of arterial perfusion to the aortic arch is required to prevent oxygen deprivation from damaging the tissues of the body. In order to provide sufficient flow to the aorta and the aortic branches the cannula must be a sufficient diameter to provide the appropriate blood flow without requiring high velocity flow. Typically, a perfusion cannula must provide between 4 to 6 liters/min arterial return flow at 60 to 80 mm HG in the aortic arch during a CPB procedure. The cannula is therefore expanded to a second diameter to allow an increase in the flow rate without an increase in the flow velocity. High velocity flow is not desirable because it may cause damage to the red blood cells and it tends to dislodge particles off the wall of the aorta. The lower the flow velocity, the less damaging to the blood cells and to the surrounding vessel.

As seen in FIG. 20, an internal lumen 36 is configured to provide cardioplegia to the body vessel simultaneously with perfusion delivery. The lumen 36 should be of sufficient diameter to provide cardioplegia flow at about 250 ml/min at around 200 mmHg pressure. A cross-sectional area in the range of 0.002 $in^2$ to 0.012 $in^2$ has been found to be sufficient to meet these criterion. As in perfusion flow, high pressure cardioplegia flow is undesirable as the cardioplegia solution may both "jet" against aortic root wall or valve tissue and may pressurize the coronary artery structure beyond normal aortic pressure, risking damage to the veins and aortic valve. Insufficient flow is also a serious defect as the heart may not be sufficiently cooled by the cardioplegia fluid, causing damage to the heart or, as above, the perfusion flow may be insufficient to still the heart. The multi-function lumen 36 may also be used to provide cardioplegia flow to the heart either intermittently or continuously.

Venting of air and fluids may also be provided by the device of the present invention. A separate vent lumen (not shown) in fluid communication with the aorta upstream of the occlusion member may be used to remove excess gasses and fluids from the surgical area to insure a deflated heart. The multi-function lumen 36 may also be used by supplying reverse pressure to the lumen 36 to remove the fluids. Once the area is sufficiently vented, cardioplegia may again be supplied to the lumen.

A serious problem with existing procedures is the danger of aortic root overpressurization. This occurs when the pressure on the upstream side of the heart reaches such a high level that the aortic valve is pushed out of its normal orientation back into the ventricle of the heart or when the coronary vessels themselves are damaged from overpressure. In order to prevent this from occurring, a pressure lumen 48 is provided in the inner tubular elongate body 44 to monitor the pressure conditions upstream of the valve. The pressure lumen may be integrally formed within the inner tubular elongate body 44 as seen in FIG. 20 or it may be contained in a separate structure maintained substantially parallel to the inner tubular elongate body 44.

The device of the present invention can also be used for imaging of the vessel interior during a surgical procedure. For example, as seen in FIG. 20, a multi-function lumen 36 is provided which can provide access to a surgical instrument such as an imaging device. The imaging device can be used to provide optical visual information as to the condition of the vessel interior or the aortic valve. Other important imaging technologies which are suited for use with the device of the present invention include sonic, RF, X-ray, MRI, EPR, ESR, gamma ray, and microwave imaging devices.

Figure 25A:
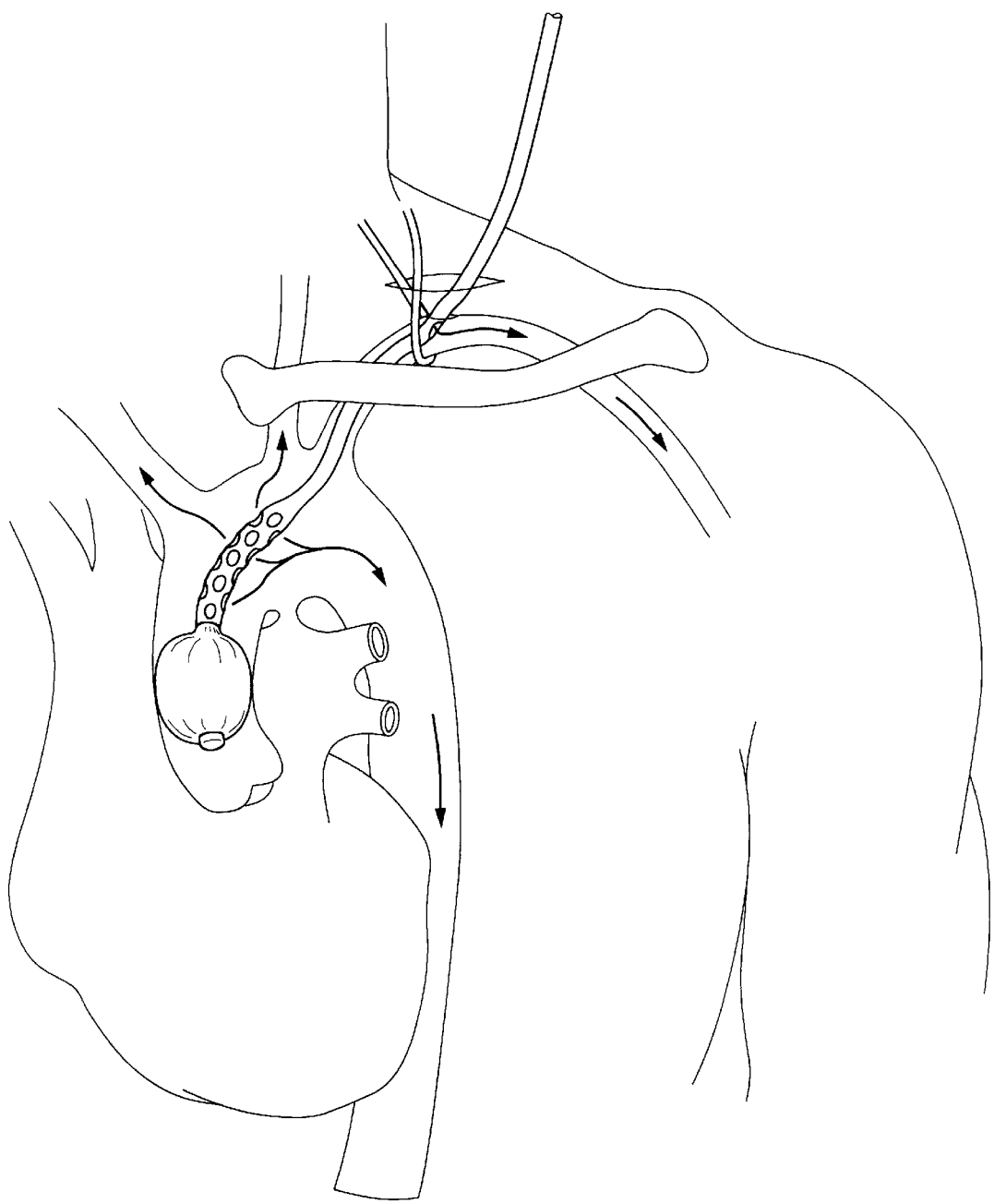
FIG. 25a shows the device of the present invention being used to access the aortic arch via the left subclavian of the patient.

In another method of use, a cannula can be configured for insertion into the right or left subclavian of the patient. Because the cannula is only 13–15 French in its unexpanded state, insertion into the narrower subclavian arteries is possible. The procedure for preparation of the percutaneous incision or direct cut-down is similar with femoral access to the aorta. The cannula is also similarly prepared for insertion into the body so that air pockets are eliminated and the device is confined to the first diameter and inserted into a resilient introducer sheath having a hemostasis valve located at the proximal end of the introducer sheath 58. Once the cannula is inserted into the subclavian artery as shown in FIG. 25a, the device is threaded into the aortic arch of the patient using the previously described methods. Once in place, the device is used in similar fashion as described above to provide arterial perfusion, cardioplegia, venting, and other functions within the aorta lumen.

In order to provide sufficient arterial perfusion downstream of the entry site, a second lumen 25b may be configured to provide flow to the patient's left side, for example, if the cannula is inserted into the left subclavian of the patient. A second cannula may also be used for supplying arterial perfusion to the subclavian artery downstream of the access site. For example, supplemental arterial supply may be required because the lumen of the left subclavian may be significantly occluded once the cannula 42 is expanded so that perfusion is prevented from flowing through the left subclavian into the left side of the body. Additionally, supplemental arterial flow can be added via a single lumen arterial return cannula through the right subdlavian, as in FIG. 26b, as the diameter of a single subclavian access site may not allow enough arterial blood flow to support the entire body.

Figure 25B:
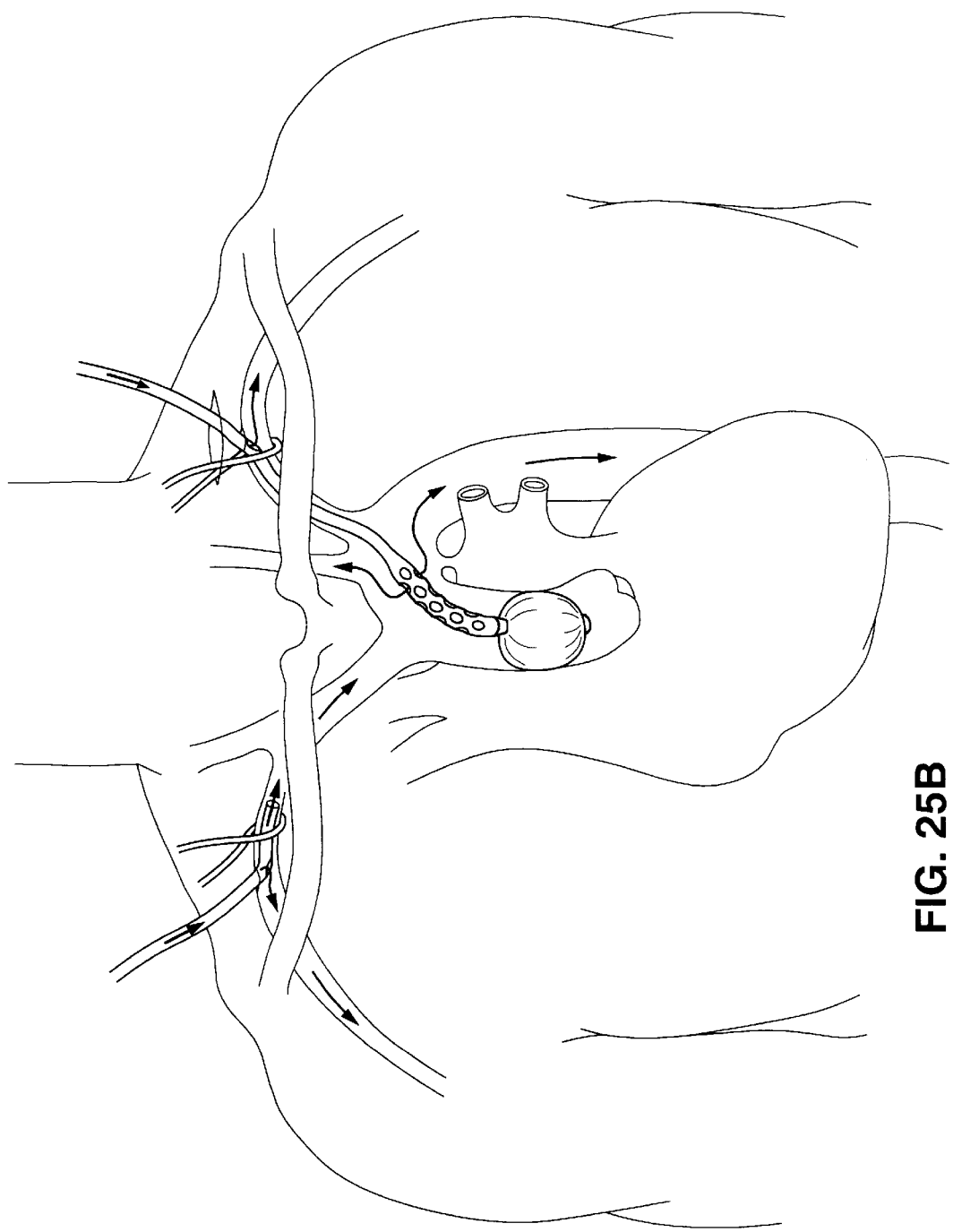
FIG. 25b shows the device of the present invention being used to access the aortic arch via the left subclavian of the patient and including a second cannula inserted into the right subclavian supplying additional perfusion flow to the aortic arch.

This supplemental flow cannula may also have a side port to allow a portion of the arterial blood to flow to the patient's right arm, since this cannula may occlude the vessel as well. This is equally applicable to access via the left subclavian as seen in FIG. 25b.

A device and methods of use for endovascular occlusion and perfusion of a body passageway has been herein described. While the particular devices and methods as disclosed are all fully capable of meeting the objects of the invention, it is to be understood that it is merely illustrative of the presently preferred embodiments of the invention and that no limitations are intended to the details of construction, design or use herein shown other than as described in the appended claims.

What is claimed is:

1. An expandable cannula for performing cardiopulmonary bypass functions in a body passageway, the cannula comprising:

an inner tubular elongate body having a distal end and a proximal end;

an outer expandable tubular elongate body expandable from a first diameter to a second diameter, the outer tubular elongate body substantially disposed-about the inner tubular elongate body, the inner tubular elongate body and the outer tubular elongate body cooperating to form a perfusion lumen within the tubular elongate body;

at least one arterial return aperture in fluid communication with the perfusion lumen provided within the tubular elongate body;

an expandable member fixed at the distal end of the inner tubular elongate body; and having an inflation lumen in the tubular elongate body in fluid communication with the expandable member; and a cardioplegia lumen with the inner tubular elongate body to provide cardioplegia flow to the body passageway.

2. The cannula of claim 1 further comprising a venting lumen within the inner tubular elongate body configured to remove excess gasses from the body passageway.

3. The cannula of claim 1 further comprising a tool lumen provided within the inner tubular elongate body, the tool lumen configured to allow insertion of a surgical tool into the body passageway to accomplish a surgical procedure.

4. The cannula of claim 1 further comprising a pressure lumen provided within the inner tubular elongate body, the pressure lumen in pressure communication with the body passageway.

5. The cannula of claim 1 wherein the inner tubular elongate body is integrally formed with the expandable outer tubular elongate body.

6. The cannula of claim 1 further comprising means for expanding from a first diameter to a second diameter comprised of a sheath disposed about the outer expandable tubular elongate body which restrains the outer tubular elongate body to the first diameter wherein removal of the sheath allows the outer tubular elongate body to expand to the second diameter.

* * * * *